(12) United States Patent
Sarver et al.

(10) Patent No.: US 7,866,820 B2
(45) Date of Patent: Jan. 11, 2011

(54) CORNEO-SCLERAL TOPOGRAPHY SYSTEM

(75) Inventors: Edwin J. Sarver, Carbondale, IL (US); James Marous, South Vienna, OH (US); Cynthia Roberts, Columbus, OH (US)

(73) Assignee: Vision Optimization, LLC, Columbus, OH (US)

( * ) Notice: Subject to any disclaimer, the term of this patent is extended or adjusted under 35 U.S.C. 154(b) by 286 days.

(21) Appl. No.: 11/830,372

(22) Filed: Jul. 30, 2007

(65) Prior Publication Data

US 2008/0018856 A1 Jan. 24, 2008

Related U.S. Application Data

(63) Continuation-in-part of application No. 11/674,985, filed on Feb. 14, 2007, now abandoned.

(60) Provisional application No. 60/773,293, filed on Feb. 14, 2006.

(51) Int. Cl.
*A61B 3/10* (2006.01)
(52) U.S. Cl. ........................ 351/212; 351/205
(58) Field of Classification Search .......... 351/210–212
See application file for complete search history.

(56) References Cited

U.S. PATENT DOCUMENTS

| | | | |
|---|---|---|---|
| 4,995,716 A | 2/1991 | Warnicki et al. | |
| 5,159,361 A | 10/1992 | Cambier et al. | |
| 5,406,342 A | 4/1995 | Jongsma | |
| 5,886,767 A * | 3/1999 | Snook | 351/212 |
| 6,024,449 A * | 2/2000 | Smith | 351/212 |
| 2002/0159618 A1 | 10/2002 | Freeman et al. | |
| 2003/0103189 A1 | 6/2003 | Neureuther et al. | |
| 2003/0227612 A1 | 12/2003 | Fein et al. | |

OTHER PUBLICATIONS

U.S. Appl. No. 11/674,985, filed Feb. 14, 2007, Edwin Sarver.

* cited by examiner

*Primary Examiner*—Scott J Sugarman
*Assistant Examiner*—Dawayne A Pinkney
(74) *Attorney, Agent, or Firm*—William Greener; Bond, Schoeneck & King, PLLC

(57) ABSTRACT

An advanced rasterstereography-based corneo-scleral topography (RCT) device includes an LED-based grid projection/illumination assembly, a grid image viewing assembly, and an optionally integratable front view camera assembly. The assemblies each include telephoto optical systems that provide a compact structure, an increased depth of field, and an increased field of view that allow sufficient acquisition of data in a single acquired image to provide the desired corneo-scleral topography analysis. The device utilizes a novel image processing algorithm. The device and method provide the capability to map a feature from a raw grid image onto a topography map of the corneo-scleral region, and to simultaneously display the images if selected by the user. The hardware, software, mechanical, electrical, and optical design considerations and integration provide advantages and benefits over prior RCT-type, Placido-based, and other conventional corneal topographers.

30 Claims, 29 Drawing Sheets

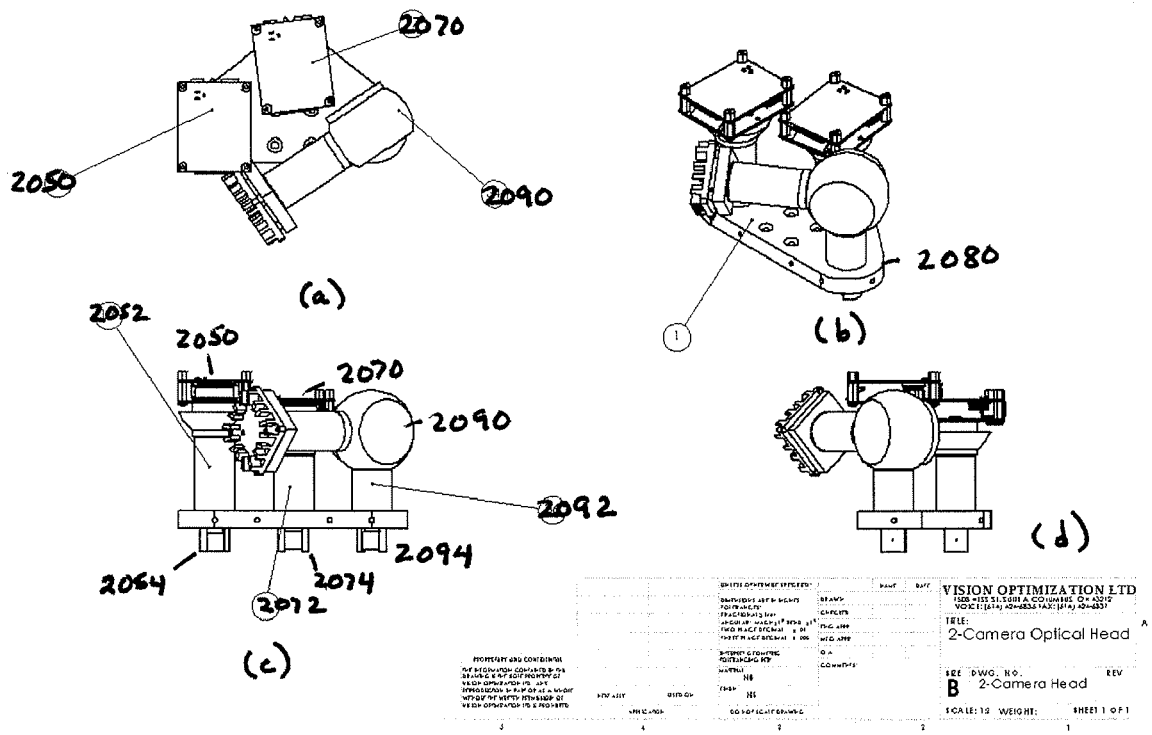
FIG 15 (a, b, c, d)

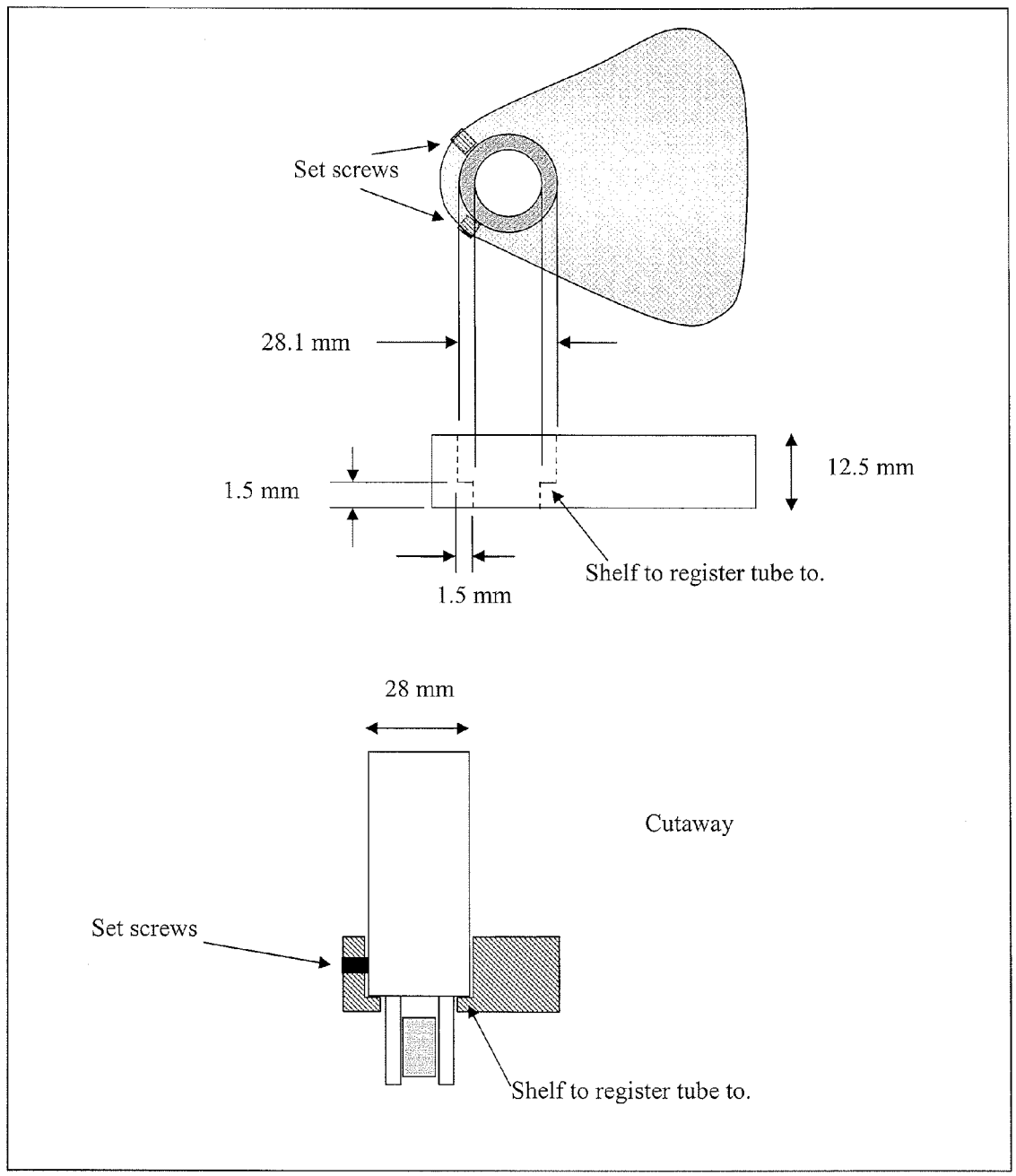
FIG. 17 a, b

Figure 22(a-d)

CORNEO-SCLERAL TOPOGRAPHY SYSTEM

RELATED APPLICATION DATA

This application is a continuation application of Ser. No. 11/674,985 filed on Feb. 14, 2007, which itself claims priority to provisional application Ser. No. 60/773,293, filed Feb. 14, 2006, the disclosures of which are herein incorporated by reference in their entireties.

FIELD OF THE INVENTION

Embodiments of the invention relate to an ophthalmic topography measurement system and, more particularly, to an advanced rasterstereography-based corneo-scleral ("RCT") topography measurement system; and to an image processing method used in conjunction with the system.

BACKGROUND OF THE INVENTION

The human cornea is the clear window of the eye. It provides as much as seventy-five percent of the refractive power of the eye; thus, it is of great interest to accurately assess the eye's topography (surface shape), and have the capability to map the topography particularly over the cornea, limbus and the neighboring scleral region. This shape information can be used to diagnose corneal disease (such as Keratoconus), plan vision correction therapies involving the use and fitting of contact lenses and in intra-operative procedures, and in other ophthalmic applications as those skilled in the art will appreciate.

Commonly used and conventional corneal topography systems include, for example, Placido-based systems that measure a concentric light ring pattern that is specularly reflected from the cornea, and scanning-slit systems. Placido-based systems often suffer from the inability to measure highly aberrated corneas, which can cause multiple reflections of the mires. Scanning slit-based systems operate by capturing individual images of a bright slit of light that is diffusely reflected/scattered from various surfaces of the eye. This diffusely reflected image does not have image edges as sharp as those of the specularly reflected mire images. As a result, the inherent measurement accuracy is reduced. In addition, since the slits must be scanned over some finite time period in which the eye can be moving, there may be problems in providing an exact registration of the individual images relative to the eye being measured.

Another topography measurement system that was commercially available in the 1990's was known as the PAR Corneal Topography System (PAR CTS). The PAR CTS is referred to as a rasterstereography-based system. Rasterstereography-based topography is a method of obtaining contour or topographic information where one of the cameras in a stereogrammetric pair is replaced with a light source, which projects a cyan grid of parallel lines onto a surface to be measured. If the topography of a cornea is to be obtained, fluorescein solution is applied onto the tear film of the cornea so that the grid pattern becomes fluorescent and can be imaged. The PAR CTS was advantageous in that its operation was not dependent on specular reflection of the grid, and therefore not dependent on high quality optical surfaces or strict alignment criteria. The PAR CTS also was an "elevation" (height) system, distinguishing it from Placido-based systems, which measure surface slope rather than elevational height directly. The interested reader is directed to U.S. Pat. Nos. 4,995,716 and 5,159,361, the disclosures of which are incorporated herein by reference in their entireties.

Although the PAR CTS was discontinued by the manufacturer in 1998, many systems were sold worldwide prior thereto, and many are still in use. Some clinicians still prefer to use the PAR CTS over other topographic systems for specific patients, despite the fact that the computer (pre-Pentium) and operating system (Windows 3.11) are, by today's standards, excruciatingly slow and cumbersome, and are no longer supported by the manufacturer.

Other recognized shortcomings of the PAR CTS were related to image processing speed and capability, and specialized image acquisition hardware having limited availability. The PAR CTS also had a long working distance and long optical layout that, made it difficult to use or integrate with surgical microscopes and other diagnostic and/or therapeutic devices, thus further limiting its utility.

Embodiments of the instant invention, described herein as an advanced Rasterstereography Corneo-scleral Topography (RCT) system, overcome the abovementioned limitations, shortcomings, and disadvantages of the prior art devices and, in particular, the original PAR CTS system. In addition, the RCT system will provide measurement and analysis capabilities that both include certain desirable features of past and currently available Placido-based, scanning slit-based, three-dimensional polar grid-based, Scheimpflug-based, or other topography measurement modalities, and others, which are not technically provided by those systems. The RCT system according to the embodiments described herein will present a modern, efficient, and efficacious device that incorporates improved hardware and software over the obsolete PAR CTS system in particular, as well as other currently available corneal topography systems.

SUMMARY OF THE INVENTION

An embodiment of the invention is directed to an advanced rasterstereography-based corneo-scleral topography (RCT) system. The system is referred to as a corneo-scleral topography system rather than merely a corneal topography system because the unique system design accommodates mapping of the cornea, limbus and neighboring scleral (hereinafter 'target') region. According to an exemplary aspect, the RCT system is equipped to project a cyan grid pattern onto the target surface in which the tear film has been stained with a fluorescein solution. The stained tear film will fluoresce and diffusely reflect/scatter the projected cyan grid, and is imaged by a grid detection camera. This diffuse reflection attribute successfully addresses the known double-reflection problem that is associated with prior art Placido-based systems. The RCT system is structurally and functionally equipped to capture a complete grid image that spans the target in a single image frame. According to an aspect, custom optics assemblies including tube-mounted imaging and grid projection systems having increased depth of field are provided. The single frame acquisition capability eliminates a need for sequential imaging and image registration, which were problematic in the prior art for sequential image systems. As described below and according to an exemplary embodiment, the RCT utilizes a customized, compact optical layout that additionally provides more efficient and improved operational integration with complementary devices such as, e.g., a surgical microscope. A modernized and more efficient, controllable LED-based illumination system is incorporated to replace the cumbersome Xenon flash system of the prior art. A controllable illumination system incorporating LEDs will allow more widespread integration of use with other diagnostic and therapeutic devices that may, for example, share wavelength requirements. Controllable LEDs will also allow illumination wavelengths that can be targeted to particular alternative fluorescing compounds, for example, Indocyanine Green (ICG), rather than the typical cyan grid/fluorescein dye combination. In another aspect, the RCT system includes a novel mapping feature that provides a visual correlation between the display of a raw grid image on the cornea and a corneal elevation or curvature map generated by the RCT system. A marker indicia on the grid image can be displayed on the elevation or curvature map. This association allows measurement features on the raw image to be viewed on the processed map. This software feature may be selectable and is useful in identifying where on the processed map physical image features are located.

According to an embodiment a novel image processing algorithm can extract and quickly process the grid features and yield an accurate and detailed corneal surface measurement, without the need for specialized image processing hardware (e.g., pc board/frame grabber) required by the prior art PAR system. According to an aspect, the total processing time for an image can be reduced to less than 2 seconds. In an exemplary aspect, the processing time for the algorithm running on a 3 GHz PC is 0.2 seconds.

According to various aspects, the embodiments of the invention incorporate components and/or design considerations that include and/or provide, without limitation thereto, the following: digital imaging capability; controlled LED Illumination; adjustable illumination levels for alignment and measurement modes; efficacious head spacing for efficient integration with other diagnostic and/or therapeutic components; full corneo-scleral coverage (up to 16.5 mm×13.25 mm); improved depth of field (e.g., $\geqq$5 mm); an adaptable core hardware platform that is modular and portable and which may include, e.g., a microscope, slit lamp; a faster, more robust grid detection algorithm; and, click-selectable raw image feature mapping/topo map overlay.

The benefits and advantages provided by the embodiments of the invention will become more apparent to a person of ordinary skill in the art based upon the following detailed description, examples and illustrations taken in conjunction with the accompanying drawings.

BRIEF DESCRIPTION OF THE FIGURES

FIGS. 15(a-d) schematically show four respective views of an optical head of the RCT system of FIG. 14;

FIG. 16b illustrates a side view of the optical assembly of FIG. 16a;

FIGS. 17(a, b) schematically show top and side views, respectively, that illustrate certain details of an optical mount according to an aspect of the invention;

DETAILED DESCRIPTION OF EXEMPLARY EMBODIMENTS OF THE INVENTION

An embodiment of the invention is directed to an image processing algorithm that involves process steps for determining the topography of a corneo-scleral target surface.

The process steps 100 of the image processing method are outlined in FIG. 1 and are discussed in detail below. In general terms, the process 100 allows one to extract the grid features from an advanced rasterstereography-based corneo-scleral topography (RCT) system captured grid image. Once the features have been extracted, the target surface topography can be reconstructed and displayed. It is particularly advantageous that the total time for processing the image can be less than 2.0 seconds. In an exemplary aspect, the processing time for the algorithm running on a 3 GHz PC is about 0.2 seconds.

Figure 1:
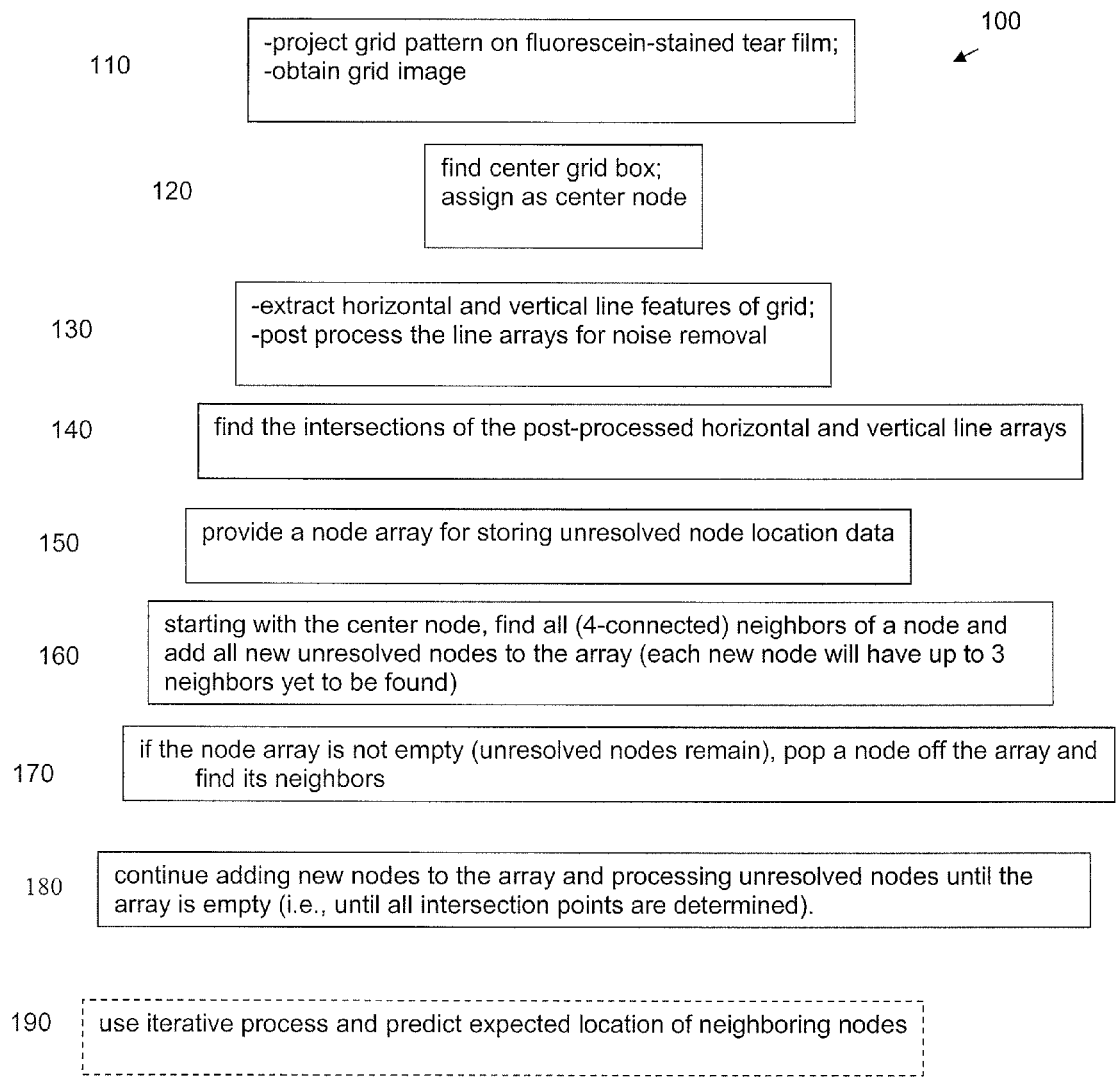
FIG. 1 is a flow diagram illustrating image processing steps according to an embodiment of the invention.

Referring to FIG. 1, at step 110 an exemplary cyan grid pattern is projected onto a fluorescein-stained tear film of a corneo-scleral surface to be measured, and an image of the fluorescing grid is obtained. The task at hand is to find the center of the grid and all grid intersections in the image. A node, as that term is used herein, is defined as the pixel space bounded by four associated intersection points of horizontal and vertical lines of the grid image.

At step 120 the center box of the grid image is detected, according to an exemplary aspect, using histograms of row and columns sums around the center of the image. This center box is denoted the center (starting) node.

Step 130 involves extracting horizontal and vertical line features of the grid image. In an exemplary aspect, the step requires enhancing the vertical lines in the image via a filtering process and saving them in an array; enhancing the horizontal lines in the image via a filtering process and saving them in an array; post-processing the vertical line array to thin the vertical lines and remove small noise features; and, post-processing the horizontal line array to thin the horizontal lines and remove small noise features.

At step 140, the intersections are found in the post-processed vertical and horizontal lines arrays.

A two dimensional node array (stack) for storing all nodes prior to resolving their pixel coordinate information is provided at step 150.

At step 160, starting with the center node, all horizontal and vertical neighbors of a node (four-connected) are found and all new unresolved nodes are added to the stack. Each new node will have up to three neighbors yet to be found.

As the nodes are resolved (described in further detail below), they are removed from the stack until the stack is ultimately empty. If the stack is not empty, a node is popped off the stack and its neighbors are found at step 170.

At step 180, new, unresolved nodes are added to the stack and processing the nodes continues until the stack is empty; i.e., until all intersection points are determined.

Step 190 is an optional processing step that discloses the use of prediction to estimate where neighboring nodes are expected to be located. By iterating over the set of found nodes and gradually relaxing processing thresholds, hard to locate node locations (for example, in areas of low contrast) may be extracted more reliably.

Image processing algorithm details will now be described.

Center Finding

Figure 2:
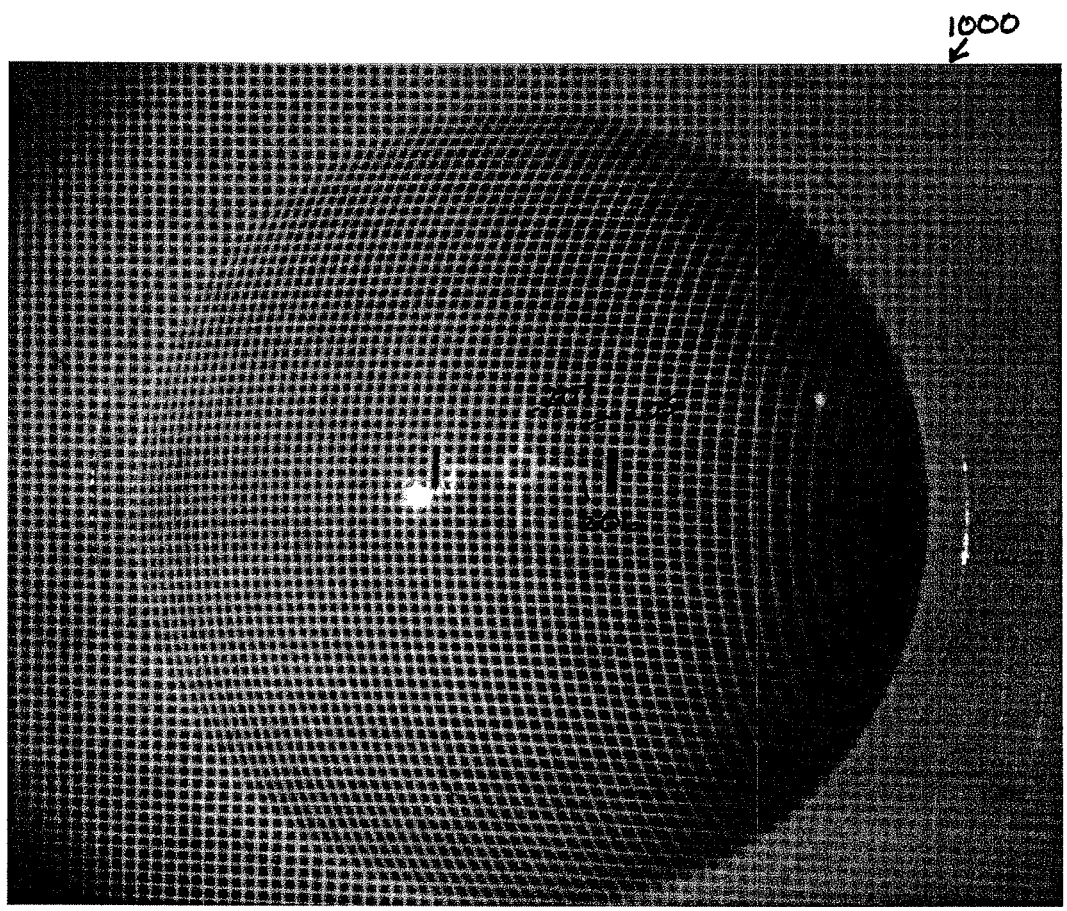
FIG. 2 shows a reticle image on an exemplary input grid image according to an embodiment of the invention.

A reticle is provided with the grid projection optics (described in further detail below) that provides a centered cross pattern 205 as shown in FIG. 2. The first step in the image processing algorithm 100 is to detect the cross pattern 205 in the image 1000 as illustrated in FIG. 2. As shown, the cross pattern is brighter and has a higher contrast than surrounding pixels. Also, the horizontal and vertical sections 206, 207 of the center cross are generally aligned with rows and columns of the image, as further illustrated schematically in FIG. 3. These characteristics are effectively exploited to properly locate the cross pattern.

Figure 3:
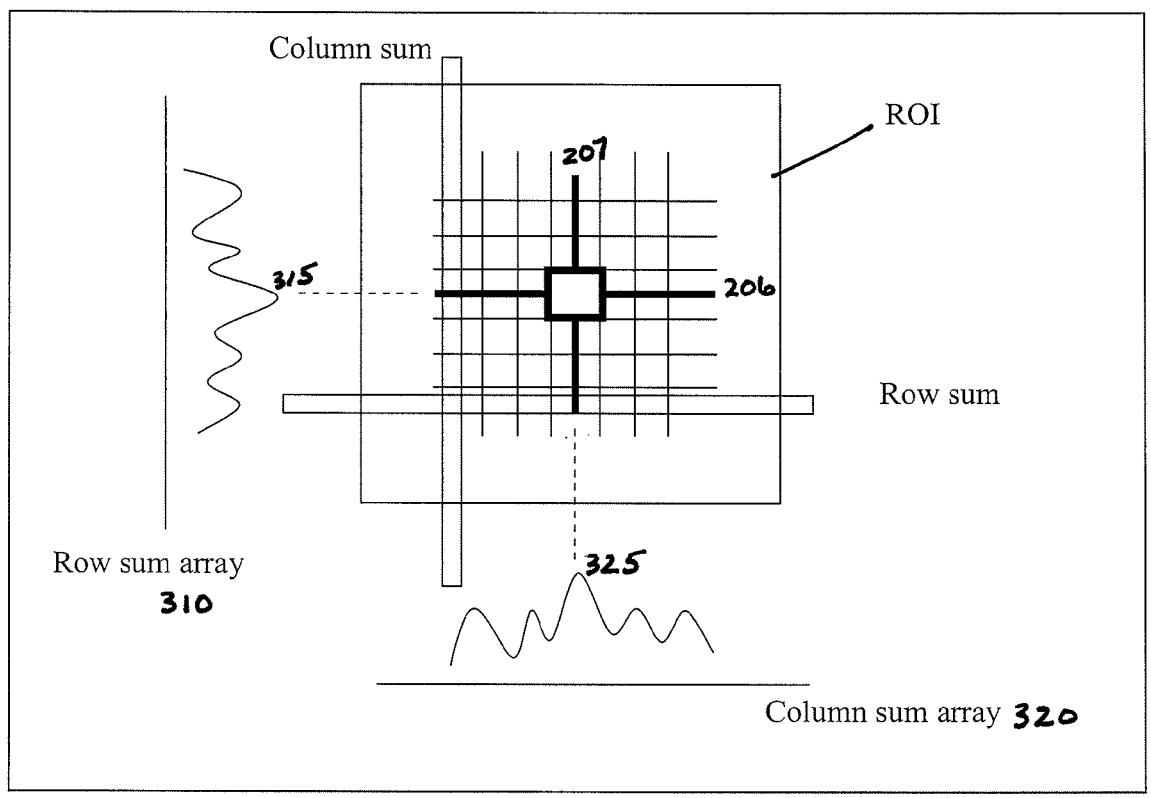
FIG. 3 is a schematic diagram useful in illustrating how row and column sums are used to find the location of the center of grid pattern according to an embodiment of the invention.

FIG. 3 illustrates the process of adding all pixels along a row inside a region of interest (ROI), representing approximately one-third of the image in an exemplary aspect, and saving the sum in a row sum array 310. The same procedure is carried out for the columns in the ROI for a column sum array 320. Once the row and column sums are found, the peaks 315, 325, respectively, are found in the arrays as the maximum values. The peak 315 in the row sum array 310 corresponds to the Y location of the cross center, and the peak 325 in the column sum array 320 corresponds to the X location of the cross center.

Figure 4:
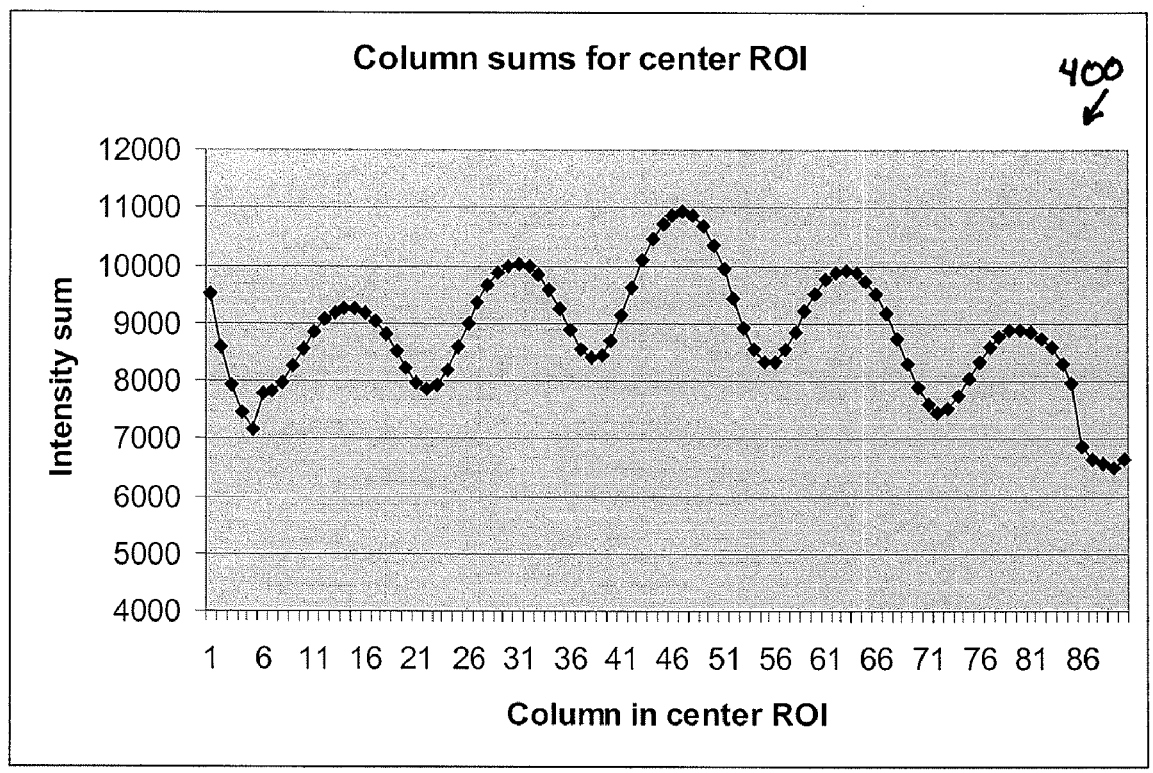
FIG. 4 illustrates a profile of column sums in a region of interest (ROI) for the image shown in FIG. 2 according to an aspect of the invention.

FIG. 4 is a profile 400 of an exemplary column sum array 320 in the center region of interest (ROI) for the image 1000 in FIG. 2. The profile of row sums (not shown) is similar.

Figure 5:
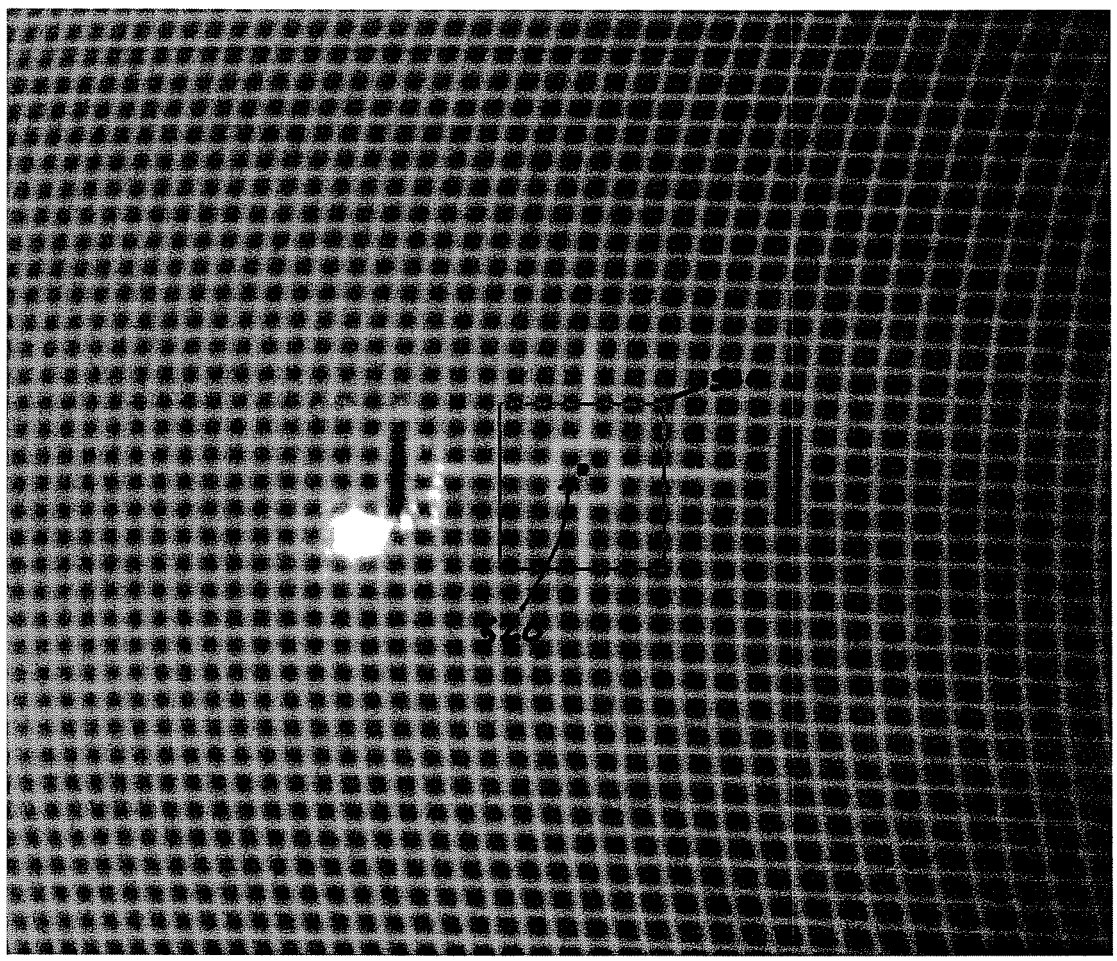
FIG. 5 illustrates an algorithmic result of center finding for the image shown in FIG. 2 according to an aspect of the invention.

FIG. 5 illustrates the results of the center finding for the image of FIG. 2. The square 510 delimits the center ROI where the row and column sums are computed. The central dot 520 shows the computed cross center.

Extraction Of Vertical And Horizontal Line Features

According to the embodiment, the next process is to extract the vertical and horizontal line features of the grid image. The first step in extracting the vertical and horizontal line features is feature enhancement. According to an illustrative aspect, a simple convolution operation is used to enhance the vertical and horizontal line features. The illustrative convolution operation merely involves a point by point multiply and add operation to determine a final value for a particular sample. Once this point is centered on the image, the edge can conveniently be determined.

In an exemplary aspect, the filter is a zero-phase FIR filter. The shape of the convolution kernel is illustrated below for the vertically oriented linear features. It is particularly advantageous in that it uses only constant values of (−1, 1). The horizontal filter is an obvious rotation of the vertical filter as would be understood by a person skilled in the art.

$$\begin{matrix} -1 & 0 & 1 \\ -1 & 0 & 1 \\ -1 & 0 & 1 \\ -1 & 0 & 1 \\ -1 & 0 & 1 \end{matrix}$$

Figure 6:
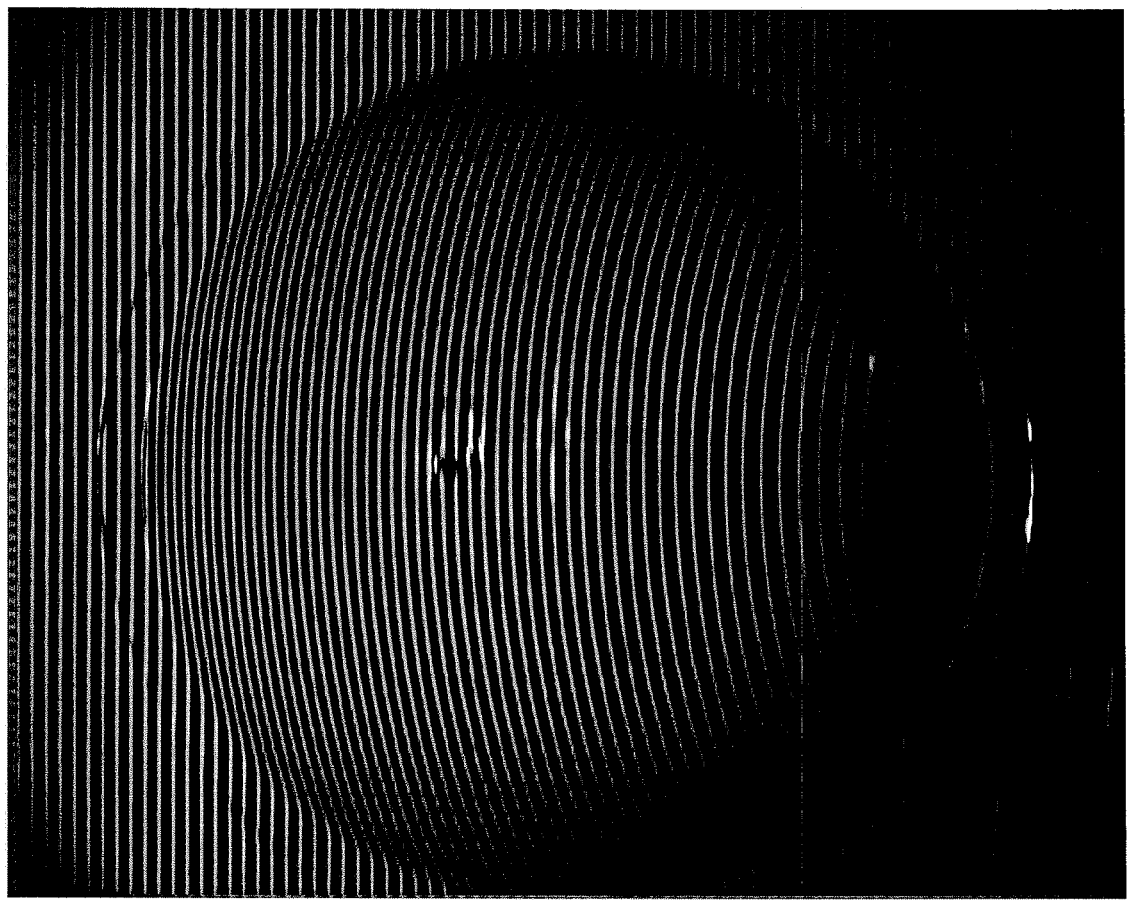
FIG. 6 shows an exemplary grid image illustrating vertical linear feature enhancement via a convolution operation according to an aspect of the invention.

The dimension of this convolution kernel is (2h+1)×3, where h is the "half-height" of the neighborhood (w=1 sample along the horizontal direction; h=2 samples along the vertical direction). Odd-lengths are used in both the height and width of this filter so as to preserve the location of the filter output. For a half-height of 8, the filter size is 17×3. The output of the filter is scaled to keep the pixel values between 0 and 255. FIG. 6 shows the results of vertical linear feature enhancement using the convolution operation described herein. Other filter types may be used, such as recursive or Fourier filters, for example. As shown in FIG. 6, the vertical (line) features are significantly enhanced. It can be noted, however, that the right hand side of the image is significantly darker (less contrast) than the left and center regions of the image.

Figure 7:
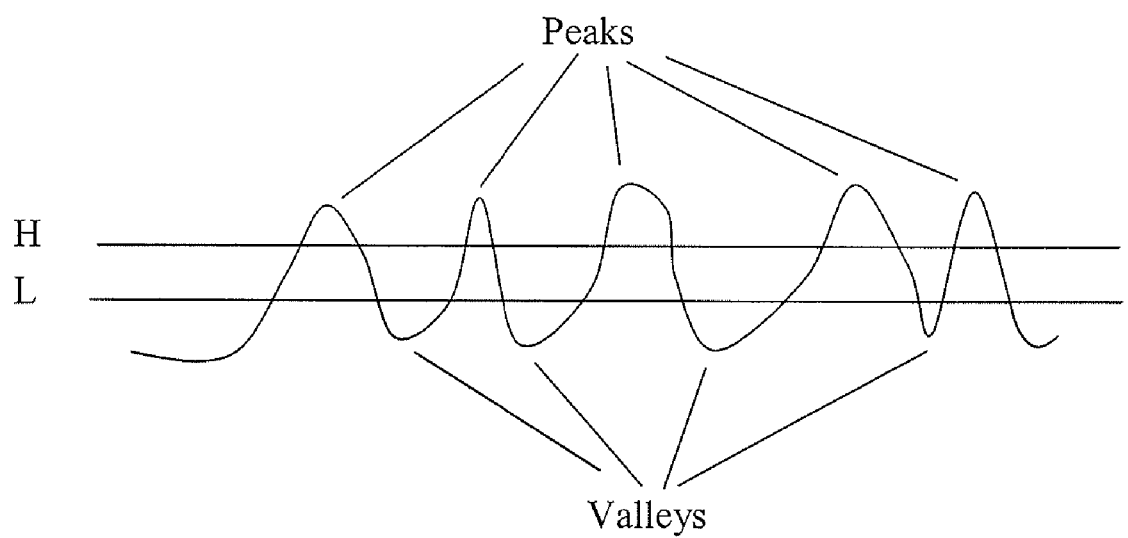
FIG. 7 is a schematic diagram that illustrates peak detection by the algorithm according to an aspect of the invention.

The next step is to scan the image to detect the peaks. According to an aspect, the peaks are adaptively determined in a way that tolerates the non-uniform illumination present in the image. A novel peak detection strategy is explained with reference to FIG. 7, where H represents a high threshold and L a low threshold, further representing the local maxima and minima, respectively.

The exemplary peak detection algorithm finds the local minima and maxima for a one dimensional profile. Two selected threshold values are used. A high threshold, H, must then be exceeded for a peak to be detected and a low threshold, L, must be exceeded in the negative direction for a valley to be detected. To compute the high and low threshold values, the algorithm sorts all values in the vector being processed and, in the exemplary aspect, takes the 45% point and 65% point as the low and high threshold values, respectively. This separation of the thresholds (as opposed to using 50% for both thresholds) provides a certain amount of noise immunity for the local minima and maxima. Other non-equal threshold values may alternatively be selected.

To provide adaptability of the thresholds across the image, the thresholds are computed over regions along the profile vector. The peak detection algorithm is applied to each row in the vertical feature enhancement image with four equally spaced sub-regions (e.g., ROI/4), where the thresholds are re-computed, according to an exemplary aspect. To each peak the algorithm assigns the value of 255, while the value of zero is assigned to all other pixels. This has the effect of thinning and "binarizing" the vertical feature enhancement image.

Figure 8:
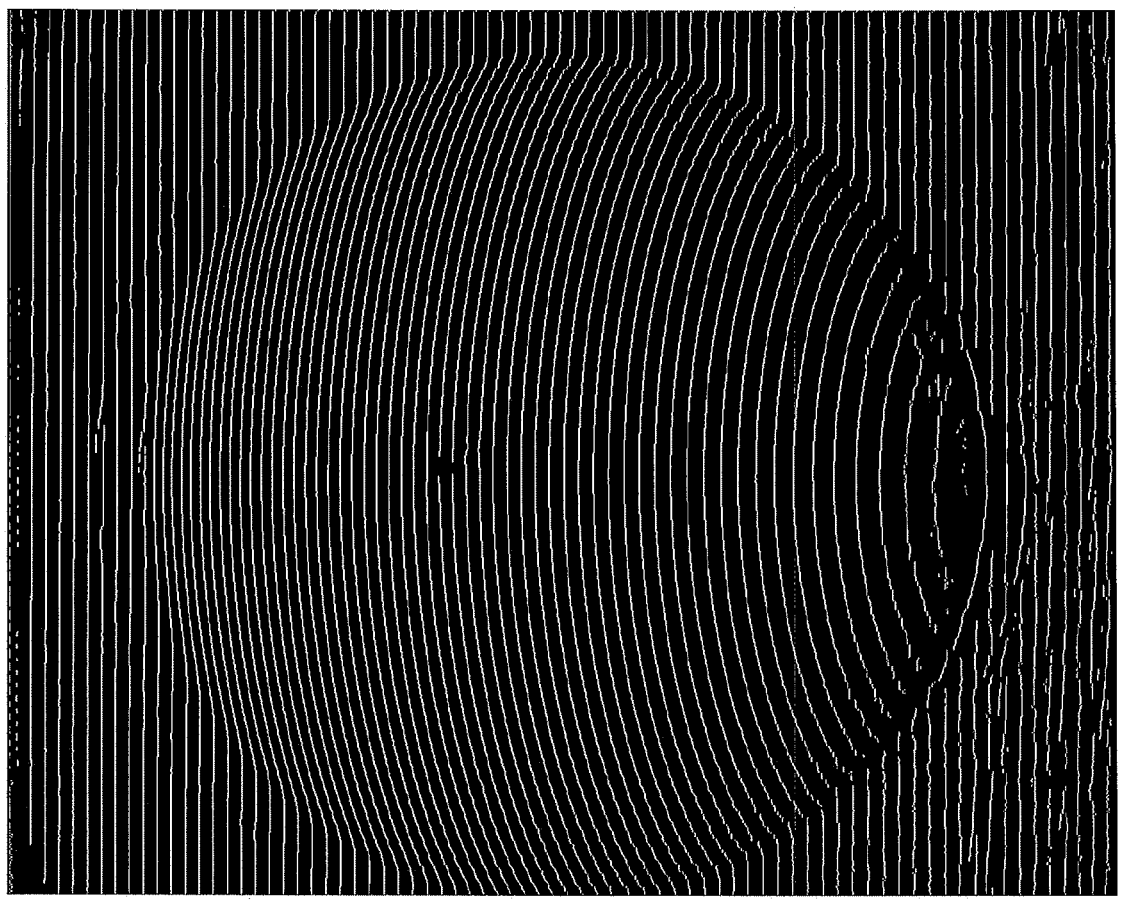
FIG. 8 shows the image of FIG. 6 after thinning, binarizing, and shot noise removal according to an aspect of the invention.
Figure 9:
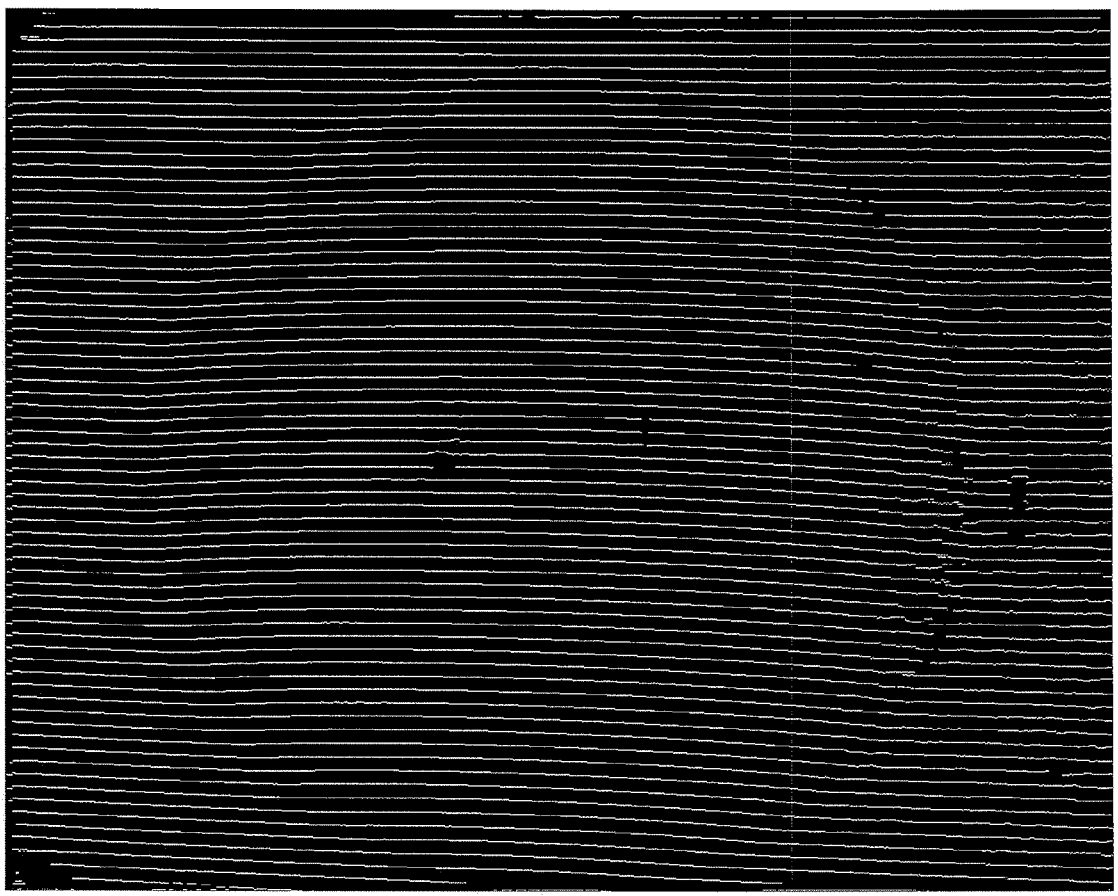
FIG. 9 shows an image similar to that of FIG. 8, which illustrates the results of horizontal features processing after thinning, binarizing, and shot noise removal according to an aspect of the invention.

Occasionally, certain vertical features in the original image will lead to small (e.g., one or two pixels) features in the thinned image. To remove these noise features, a standard "shot noise" removal filter may be used. In this filter, the neighborhood around a pixel is searched. If it is surrounded by zero values, the pixel value is set to zero. The final result of the vertical features processing is shown in FIG. 8. The processing result for the horizontal features is shown in FIG. 9, corresponding to the image shown in FIG. 8.

Finding Grid Image Intersections

In the next step of the algorithm, the intersection points of the vertical and horizontal thinned grid images are found. For most pixels, this is a simple matter of checking that the value of a pixel in both images is 255. However, it is possible that due to the manner in which the continuous linear features are made discrete, that a vertical and horizontal line will actually be present, but the intersection will not be detected. This can happen, e.g., when the continuous horizontal linear feature has a slight positive slope, the continuous vertical linear feature has a nearly vertical negative slope, and the continuous lines just happen to cross at the boundary of a pixel. This is illustrated in FIG. 10.

Figure 10:
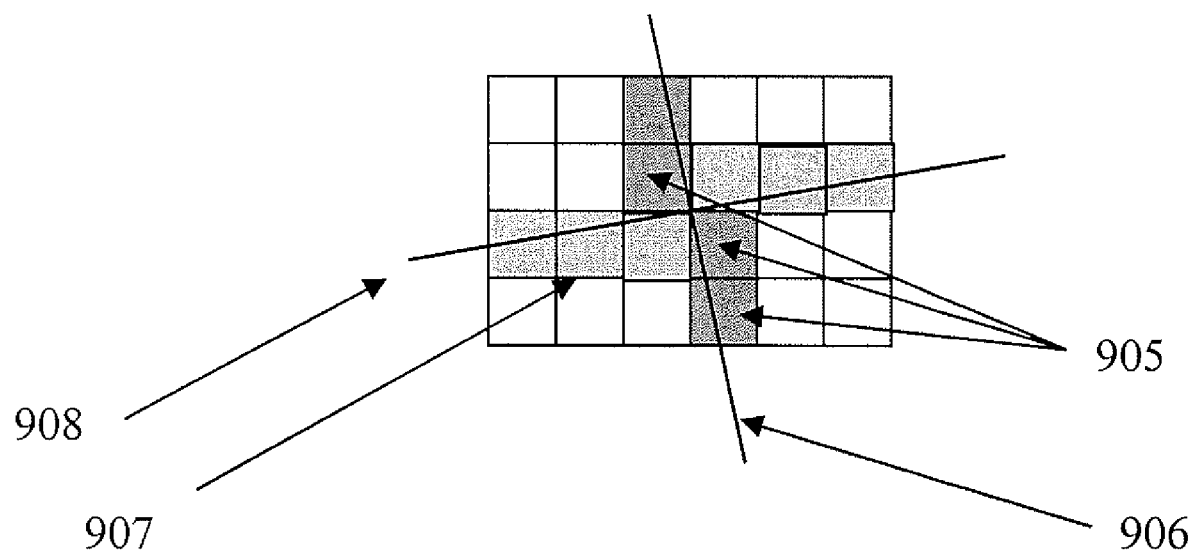
FIG. 10 is a diagram that illustrates an exemplary instance when a continuous horizontal linear feature and a continuous vertical linear feature cross at the boundary of a pixel.
Figure 11:
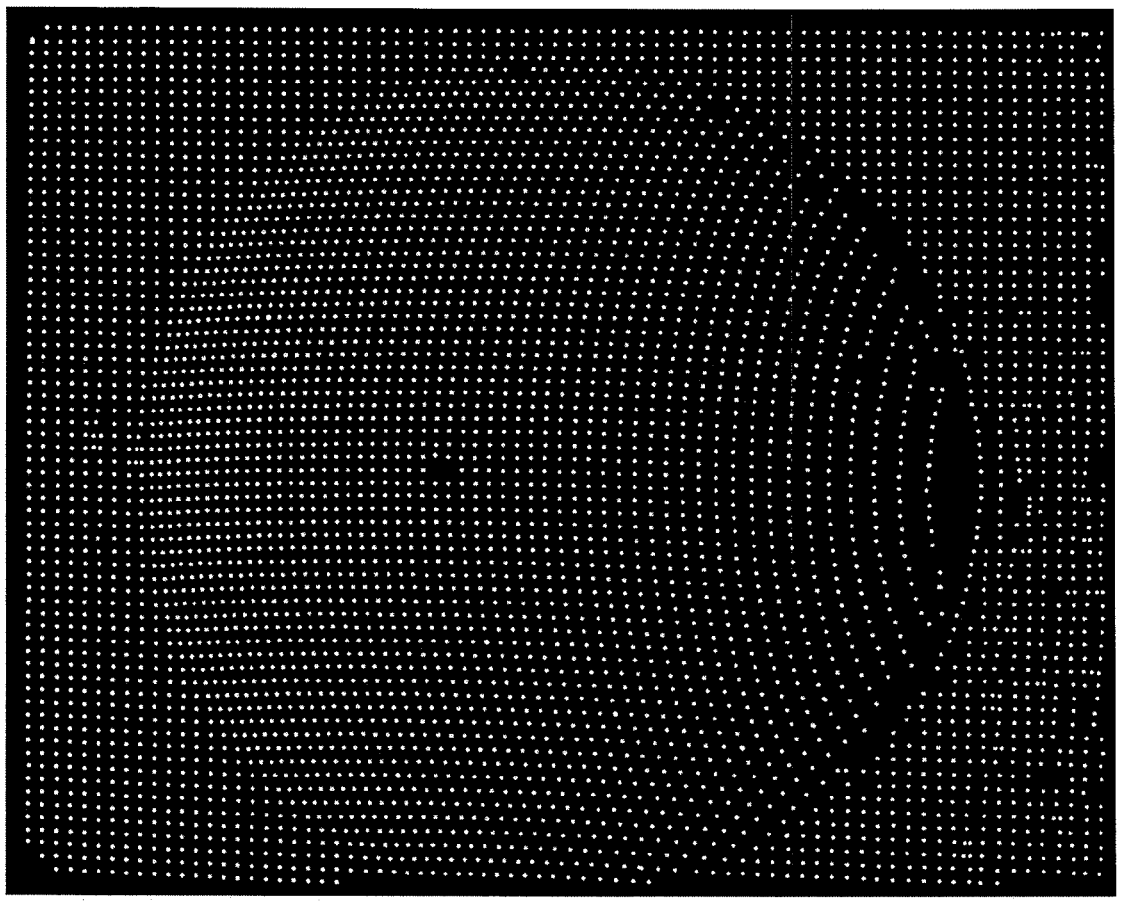
FIG. 11 shows an exemplary image illustrating the intersections of the vertical and horizontal line features as depicted in FIGS. 8 and 9 according to an aspect of the invention.

In FIG. 10, the darker (vertically-oriented) squares 905 represent a discrete version of the vertical line 906 and the lighter gray squares 907 represent a discrete version of the horizontal line 908. Although the linear features (906, 908) actually intersect, the discrete pixels do not have the same pixel in common indicating the intersection in the simple test described above. The probability of this occurring at a node is very low, but since there are over 1,000 nodes to process, it may occur one or more times per image. The situation may also occur when the continuous horizontal linear feature has a slight negative slope, the continuous vertical linear feature has a nearly vertical positive slope, and the continuous lines just happen to cross at the boundary of a pixel. To handle these situations, the line intersection test is modified as follows:

The current pixel being considered is at "00". Let the pixel values for a 2×2 neighborhood in the vertical thinned image be V00, V01, V10, and V11. The corresponding horizontal thinned image pixel values are H00, H01, H10, and H11. If V00=H00=255, the lines intersect; or if V00=V11=H01=H10=255, the lines intersect; or if H00=H11=V01=V10=255, the lines intersect. Using these digital line intersection rules, the output image from the thinned images in FIGS. 8 and 9 is shown in FIG. 11. In the image of FIG. 11, the spots have been greatly expanded in size for viewing. In the actual image, each dot is a single pixel.

Finding Four-Connected Node Neighbors

After the center of the cross has been found (as shown in FIG. 5) and the linear feature intersections are located (illustrated in FIG. 11), the next step is to find the nodes. Each node will be considered to contain a "Point" object. A Point object holds the (x,y) pixel location of the node. The nodes are stored in a two-dimensional array so that it is easy to find the neighboring nodes. According to an exemplary aspect, the size of the node array is 101×101 (based on grid size and eye magnification). Thus, the center node is located at element 50×50. The array is indexed Nodes [x, y] where x indicates the column (center is 50), and y indicates the row (center is 50). The node to the right of the center node would be stored at index (51,50) therefore x increases to the right. The node above the center node would be stored at index (50,49), y increasing in the downward direction. At each array sample the algorithm stores the pixel location of the node. If the pixel location of the center node (center of the cross) is 640, 512, then Nodes [50,50]=Point (640, 512).

When the Nodes array is created, all node values are assigned Point (0,0). The algorithm uses this value to indicate a node that has not yet been found (i.e., resolved). A node can be deleted simply by overwriting its pixel location with Point (0,0). For a given node, the 4-connected neighbors are those to the right, above, left, and below. The 8-connected neighbors would include those in the diagonal directions from the center node. In the center of the image, the grid intersections are almost regularly spaced. This attribute of the image can be exploited by searching a fixed distance from the center node to where the neighboring node is expected to be. This is illustrated with reference to FIG. 12.

Figure 12:
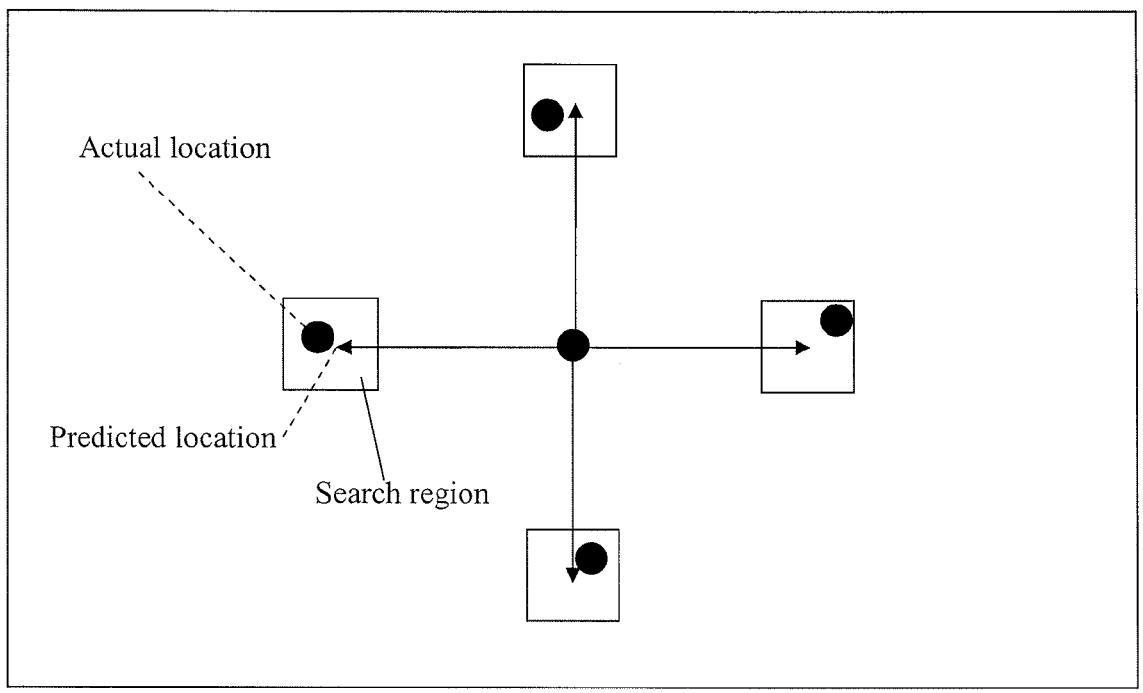
FIG. 12 is a schematic diagram that is used to illustrate the process of searching for nodes according to an aspect of the invention.

As schematically shown in FIG. 12, in the center region illustrated, the nodes are almost regularly spaced so that the algorithm can predict where the neighbors should be located with little difficulty. The predicted location is searched looking for an intersection as shown in FIG. 11. The closest pixel found to the predicted location is used as the actual location of the neighbor.

As each direction is searched for a neighboring node, the following steps are performed:
if the node is already found in a given direction, the node is not searched again;
if the node has not yet been found (it has value Point (0,0)), the algorithm searches for the node;
if the new neighbor node is found, its location is saved in the Nodes array. The node is also pushed onto the stack to look for the new node neighbors.

The pixel value is set in the intersection image (and the pixels in the immediate neighborhood) to zero so as to prevent accidentally assigning another node to the same intersection in subsequent searches. Initially, the center node is pushed onto the stack and then the process executes the neighborhood finder until the stack is empty.

When the stack is empty, it is fair to assume that not all nodes would have been found (unless the image was for a flat plane). A second pass is made over the nodes where the algorithm uses the location of found node neighbors to predict where missing neighbors should be. This provides adaptability to handle the cases where:

the nodes are close together in the x-direction but far apart in the y-direction, as in the left side of the image in FIG. 11; the nodes become far apart as in the right side of the image in FIG. 11; the node paths curve as in the right side of the image in FIG. 11 and along the edges of the sphere.

At each subsequent pass, the search window is continually increased about the predicted node location (by two pixels) until all reasonable nodes have been found. The final results are illustrated in FIG. 13.

Figure 13:
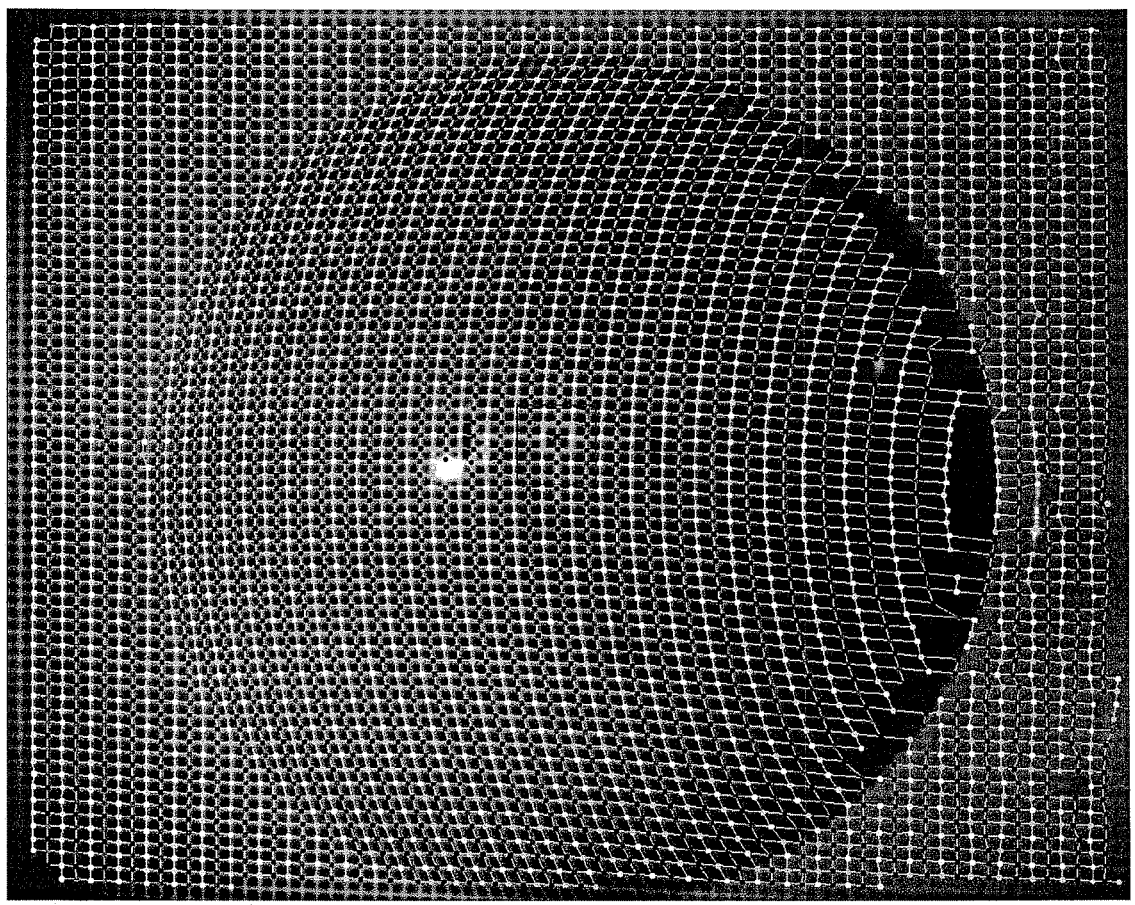
FIG. 13 shows an exemplary image that illustrates the final results where found nodes overlay the original image according to an aspect of the invention.

In FIG. 13, the nodes alternate in color (or contrast) between rows and columns to show proper topology of the nodes. A common processing error is to assign a node to the wrong row or column. The cyan connecting lines also help show that the nodes were properly placed in the correct relationship to their neighbors.

While the above described exemplary processing algorithm is fast and reasonably robust, it is anticipated that certain image artifacts will cause errors which could propagate through the reconstruction processing to yield a surface representation that is not correct in certain areas of the image. The effects of these errors can be mitigated by the use of a post-processing step that looks for neighbors which appear to be too close, too far, or at too big an angle, with respect to neighbors, as one skilled in the art would appreciate. Once a neighborhood with artifacts such as these are found, the nodes can be easily deleted by setting the node value to Point (0,0). An editor may also be provided to allow automatic or manual removal of the problem nodes.

Figure 14:
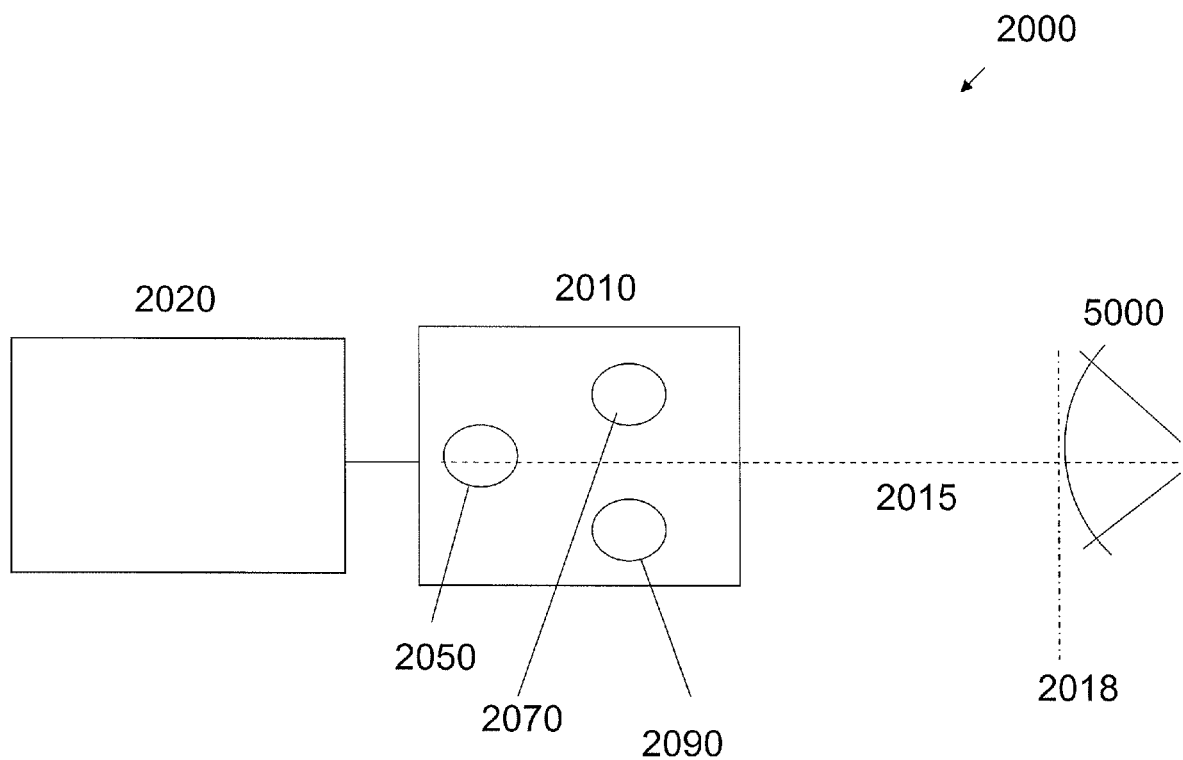
FIG. 14 shows a top plan schematic of an advanced RCT system according to an embodiment of the invention.

Another embodiment of the invention is directed to an advanced RCT system 2000 shown in an exemplary aspect in a top view illustrative schematic in FIG. 14. The RCT system 2000 comprises an optical head 2010 operationally connected to a controller/processor component(s) 2020. The optical head 2010 includes a grid optical assembly (camera/detector/optics) 2050 aligned with a target 5000 along a system optical axis 2015; a front-view optical assembly 2070; and a grid projector assembly 2090. The target surface has a location denoted by 2018. FIGS. 15(*a-d*) show four respective schematic views of the optical head 2010.

Optomechanical Layout

Figure 16A:
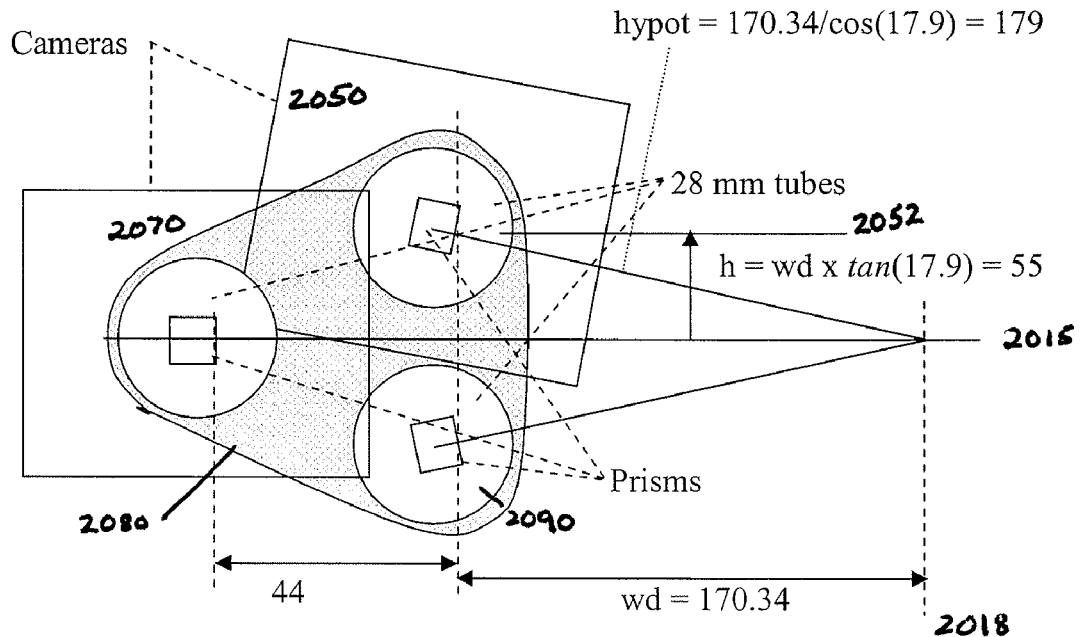
FIG. 16a schematically illustrates a top plan view of an optical assembly according to an exemplary embodiment of the invention.
Figure 16B:
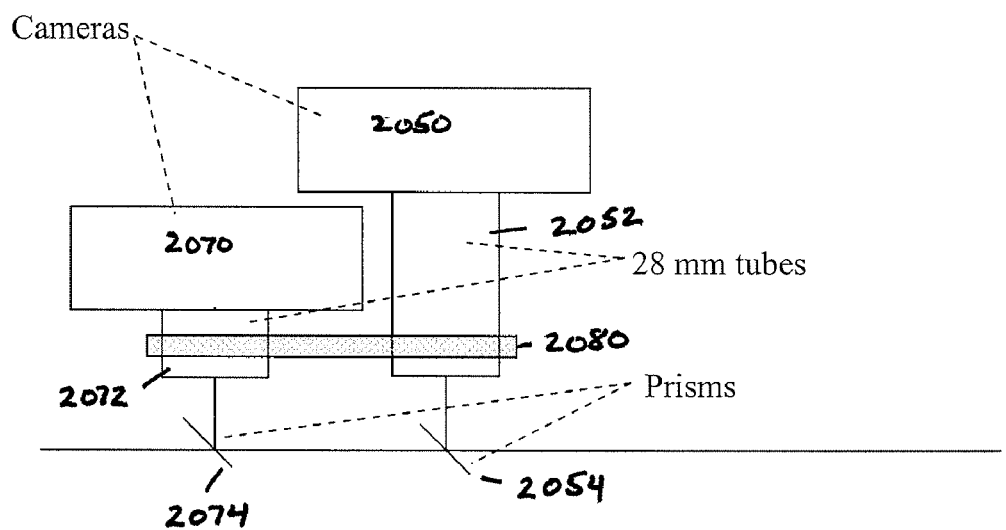

FIGS. 16(*a,b*), respectively, show further plan and side schematic views of the optical head assembly in an exemplary aspect. Referring to FIGS. 15*c* and 16*b*, the optical assemblies of the grid camera assembly 2050 and front-view camera assembly 2070 each include an imaging optics enclosure 2052, 2072, and a prism 2054, 2074, respectively. Similarly, the grid projector 2090 as illustrated in FIGS. 15(*b-d*) includes a grid projection optics enclosure 2092 and a prism 2094. The prisms provide optical path steering between the target, the cameras, and the grid projector. The optics enclosures 2052, 2072, 2092 house optical assemblies as further described below, and are in the form of tubes.

According to an exemplary aspect, FIG. 16*a* shows the distance h from the system optical axis 2015 to the center of the grid camera tube 2052, given the full angle between the grid projector 2090 and grid camera being 35.8 degrees and the working distance from the plane containing the prisms to the target plane 2018 being equal to 170 mm. Thus, raw grid measurement data is obtained at an angular displacement in the horizontal plane. From the top view of FIG. 16*a*, the extent to which the cameras 2050, 2070 overlap each other is shown, but from the exemplary side view of FIG. 16*b*, it can be seen that the front view camera 2070 is 40 mm lower than the grid view camera 2050. The respective optical imaging lenses and apertures are enclosed in 28-30 mm diameter tubes 2052, 2072. The prisms 2054, 2074 are contained in an enclosure similar to that of the original PAR design. The gray region 2080 in the top and side views is one possibility for providing a support structure for the three optical assembly tubes. Two of these triangular shapes can be aligned with standoffs to form a triangular cage. Set screws in the corners hold the optics tubes as illustrated in FIGS. 17(*a, b*).

According to an aspect, the front view camera assembly (camera, optics/enclosure, prism) may not be required and, therefore, need not be integrated. This may occur, for example, if the optical head is connected to a microscope or laser system, as opposed to being a stand-alone system. In the exemplary aspect, the distance between the center of the holes for the grid camera and grid projector is 110 mm, as shown in FIG. 16*a*.

Mounting details of an exemplary aspect is further shown in FIGS. 17(*a, b*). Optical parts were primarily assembled from off the shelf components. The tubes are 28 mm OD and 25 mm ID. The prisms are held in place by a clevis mount at the end of the optical tube. The prism was fixed relative to the camera optics in the optical tube. The rotation of the prism to be aimed for the 17.8 deg angle was made by inserting the tube into the triangular frame, twisting the tube to the correct alignment and fixing the position with two set screws as illustrated in FIG. 17*a*.

Optical/Camera Hardware System

An advantageous aspect of the embodied RCT system is the comparatively shortened overall layout, as well as the device capability to measure and analyze the topography of the cornea, limbus and neighboring scleral region, rather than just over the corneal surface. In an exemplary aspect, a telephoto lens design (positive lens followed by negative lens) was used. One criteria for the optical layout was that no vignetting of the images would be allowed. A front view (at 710 nm) for focusing and pupil acquisition was provided by a USB 2 camera. The image sensor is 6.6 mm×5.3 mm (8.46 mm diagonal). The grid reticle is chrome on glass with a 0.009 mm line width, 0.075 mm line spacing, and 19 mm in diameter. The optics are designed so that, at the target plane, the grid is 0.018 mm line width, 0.15 mm line spacing, 20 mm diameter; thus more than sufficient to overlay the corneoscleral region. The view of the corneo-scleral target surface is such that the coverage is 16.5 mm×13.25 mm (21.16 mm diagonal—10.58 mm half diagonal). This scope of target coverage is unparalleled in the art. The telephoto optical systems in conjunction with the limiting apertures also provide the generous depth of field, which equals or exceeds 5 mm, and which is not found in conventional corneal topography systems (typically 3 mm). The capability to map the cornea, limbus and neighboring sclera provides otherwise unavailable data that can be particularly useful for fitting contact lenses and/or in intra-operative procedures, and other applications. The angle between the projection and measurement arms is 12 degrees. The nominal working distance is 175 mm.

Front View Camera

Figure 18:
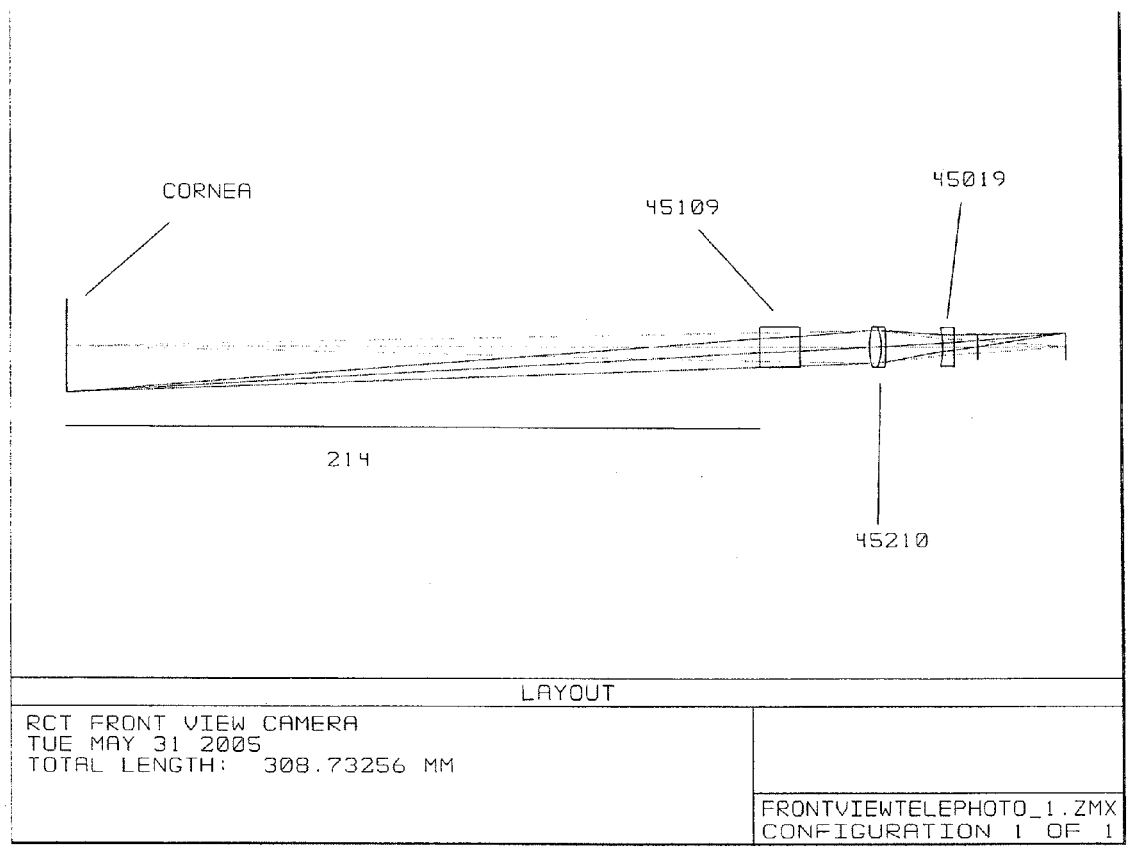
FIG. 18 shows a schematic diagram of a Zemax optical analysis ray tracing of a front view camera according to an embodiment of the invention.

The Zemax optical design layout for the exemplary front view camera 2070 is shown in FIG. 18. A 16.5×13.25 mm target surface region at the corneal plane is imaged onto a 6.6×5.3 mm camera sensor via the two element telephoto lens consisting of a +35 mm lens (45210) and a −48 mm focal length lens (45019). The distance from the corneal plane to the front of the right angle prism (45109) is 214 mm. This is 40 mm longer than the grid camera working distance so that the physical extent of the cameras (41 mm high, tapered) will not interfere with each other. The distance between the edge of the prism and the positive lens is 10 mm. The distance between the positive and negative lenses is 11.5 mm. The distance between the negative lens and the image plane is 59.5 mm. The maximum diameter of the corneal region of interest is 21.16 mm.

The Zemax ray tracing indicates that no vignetting occurs for up to a 10 mm aperture at the positive lens. The overall magnification of the front view camera is −0.4 (−0.3946).

Grid Camera

Figure 19:
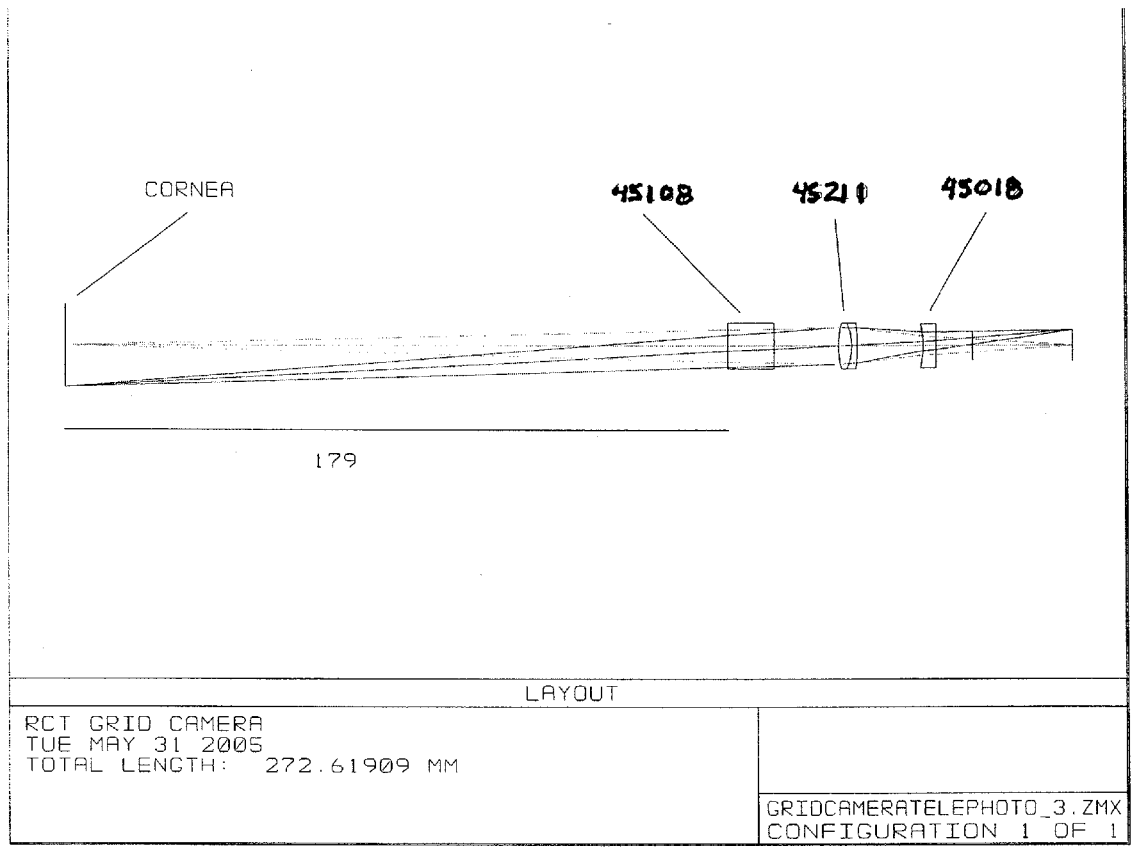
FIG. 19 shows a schematic diagram of a Zemax ray tracing of the grid camera according to an embodiment of the invention.

The Zemax layout for the exemplary grid camera is shown in FIG. 19. A 16.5×13.2 mm region at the corneal plane is imaged onto a 6.6×5.3 mm camera sensor via the two element telephoto lens consisting of a +35 mm lens (45211) and a −48 mm focal length lens (45018). The distance from the corneal plane to the front of the right angle prism (45108) is 179 mm. The distance between the edge of the prism and the positive lens is 10 mm. The distance between the positive and negative lens is 17.5 mm. The distance between the negative lens and the image plane is 39.74 mm. As before, the maximum diameter of the corneal region of interest is 21.16 mm.

The large corneo-scleral target areas are made available by the increased depth of filed provided by the telephoto lens and aperture designs. According to an exemplary aspect, the depth of field of the grid camera is equal to or greater than 5 mm.

The Zemax ray tracing again indicates that no vignetting occurs for up to a 10 mm aperture at the positive lens. The overall magnification of the grid view camera is −0.4 (−0.4041).

Grid Projector

Figure 20:
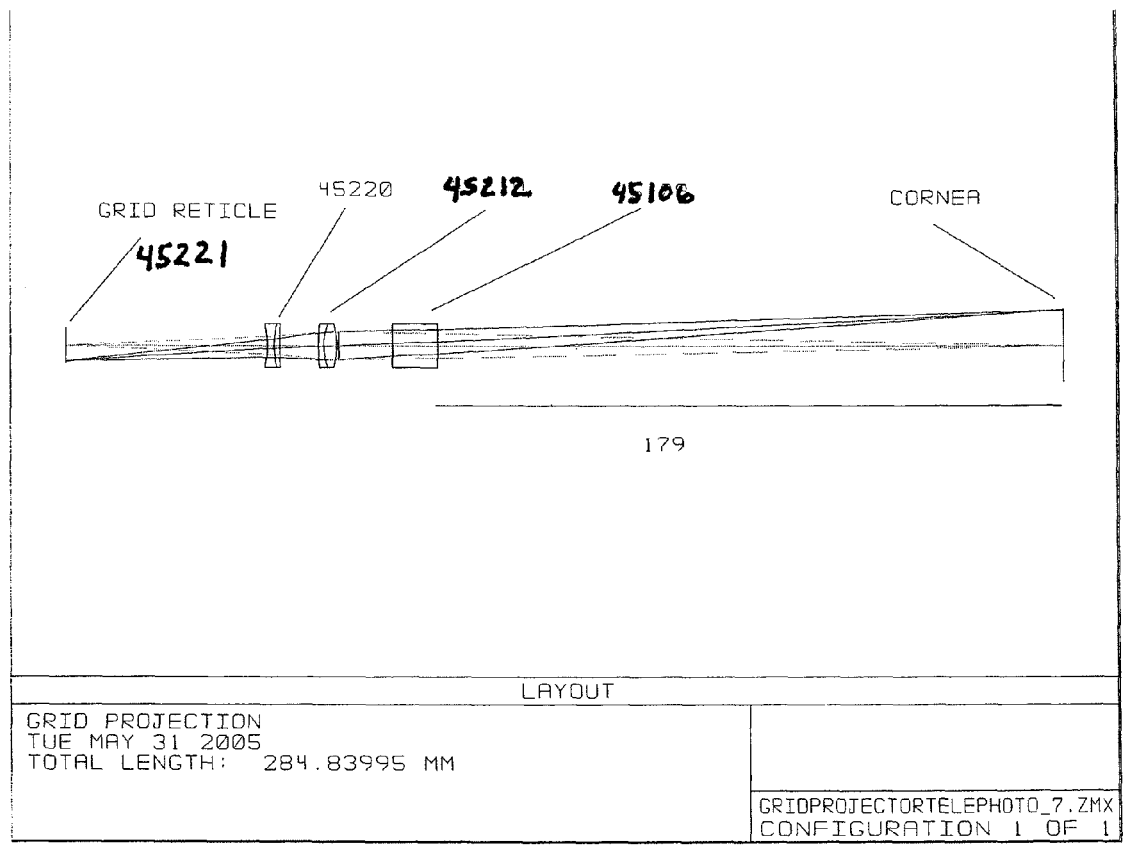
FIG. 20 shows a schematic diagram of a Zemax optical analysis ray tracing for the grid projection according to an embodiment of the invention.

The Zemax ray tracing for the grid projection is shown in FIG. 20. A 10 mm diameter region of the grid reticle (45221) is imaged onto a 20 mm diameter (plus projection distortion) via the telephoto lens consisting of a −48 mm (45220) lens and a +35 mm (45212) lens. The distance from the grid to the negative lens is 62 mm. The distance between the lenses is 10.5 mm. The distance between the positive lens and the prism (45106) is 10 mm. The distance from the prism to the corneal plane is 179 mm, which is the same as for the grid camera. The overall magnification of the grid projection is −2.0 (−2.06).

Grid Illumination

Figure 21:
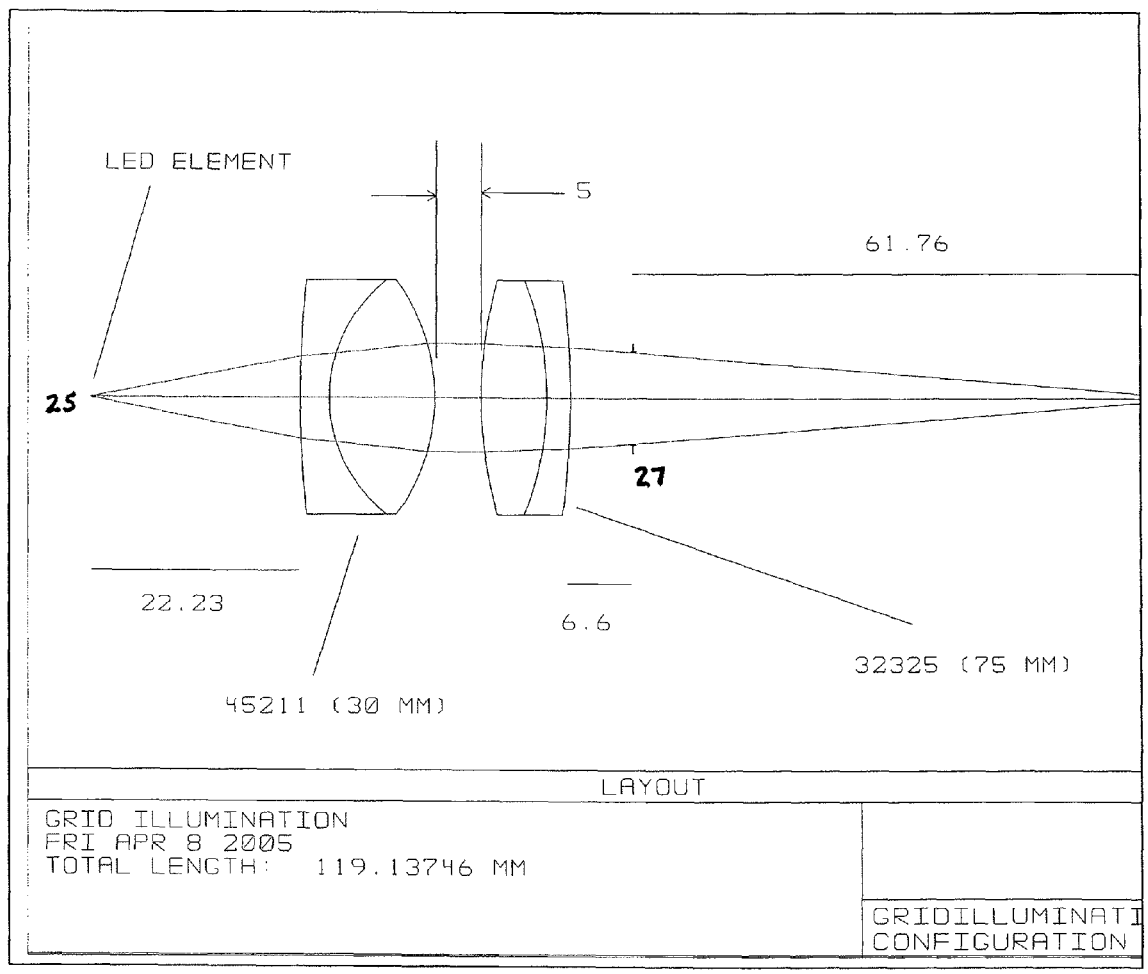
FIG. 21 shows a schematic diagram of a Zemax optical analysis ray trace for a grid illuminator according to an embodiment of the invention.

The exemplary grid illumination system is shown in an optical schematic in FIG. 21. It consists of a 1 watt LED with its integral lens ground off so that the lens system can provide a uniform illumination pattern at the grid reticle. The LED was mechanically mounted to an aluminum heat sink. The LED may be directly attached to the heat sink as the bottom of the LED package is electrically isolated from the contacts on top of the package. The LED is imaged onto the plane of the first grid projector lens via a 30 mm collimation lens (45211) and a 75 mm focusing lens (32325).

The grid reticle image 27 is 6.6 mm from the focusing lens. If the back surface of the lens and the grid reticle are at the same location, any dust on the focusing lens will be projected at the cornea. Since the distance is 6.6 mm, this artifact is avoided. The distance S from the LED element to the collimation lens is 22.23 mm. The distance between the lenses is about 5 mm. The distance from the focusing lens to the first grid projection lens is 68.37 mm.

All orientation configurations of the collimation lens and the focusing lens were evaluated and the orientation shown in FIG. 21 provided the minimum aberrations.

The LED illumination feature provides instrumentation capability not associated with earlier generation corneal topography systems. For example, the combination of a cyan grid and fluorescein dye may not be optimum under all contemplated conditions of use of the RCT system. It may be desirable to illuminate the target surface with IR light, in which case the use of a fluorescent substance such as Indocyanine Green (ICG) in place of fluorescein dye may be advantageous. Thus the capability for selecting an appropriate illumination wavelength can be provided by the LED illumination system of the RCT apparatus. More generally, the controllable LED illumination system according to an embodiment of the invention allows a particular fluorescent compound to be targeted by an appropriate corresponding illumination wavelength.

Overlay Feature

Figure 22:
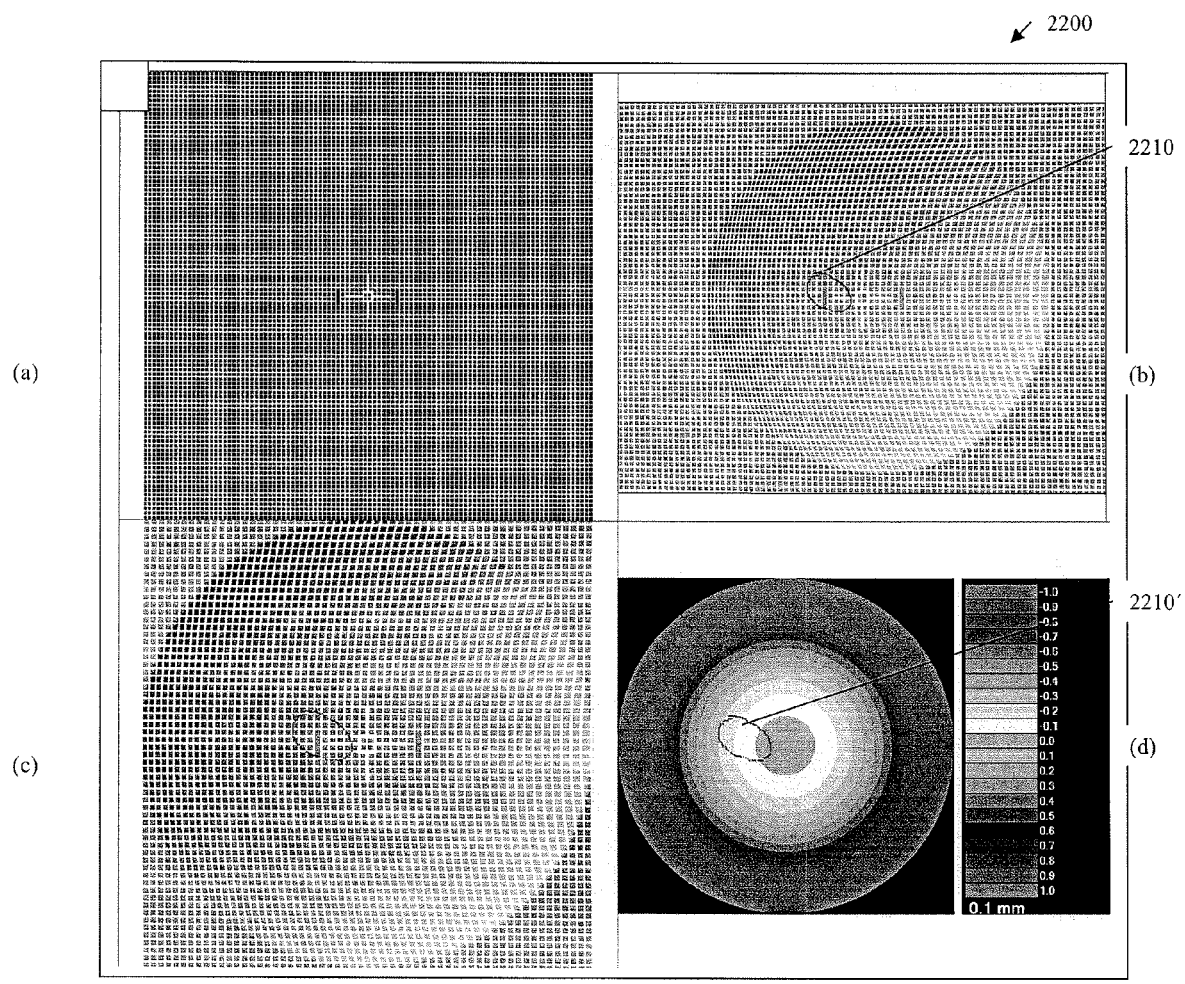
FIGS. 22(a-d) illustrate a raw data/topo map overlay feature of the RCT system according to an aspect of the invention.
Figure 23:
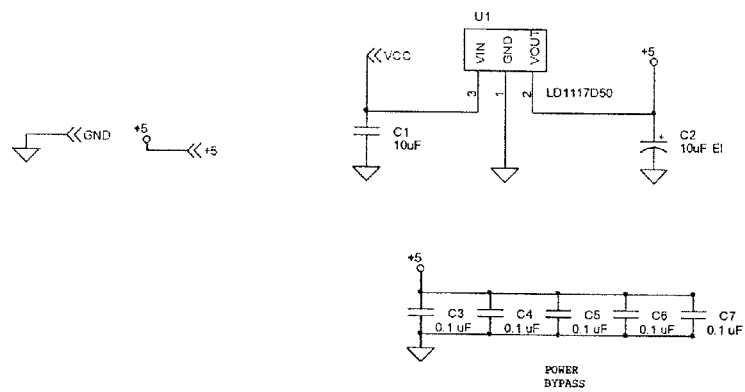
FIG. 23 is a schematic for a voltage power supply in a flash controller according to an exemplary embodiment of the invention.
Figure 24:
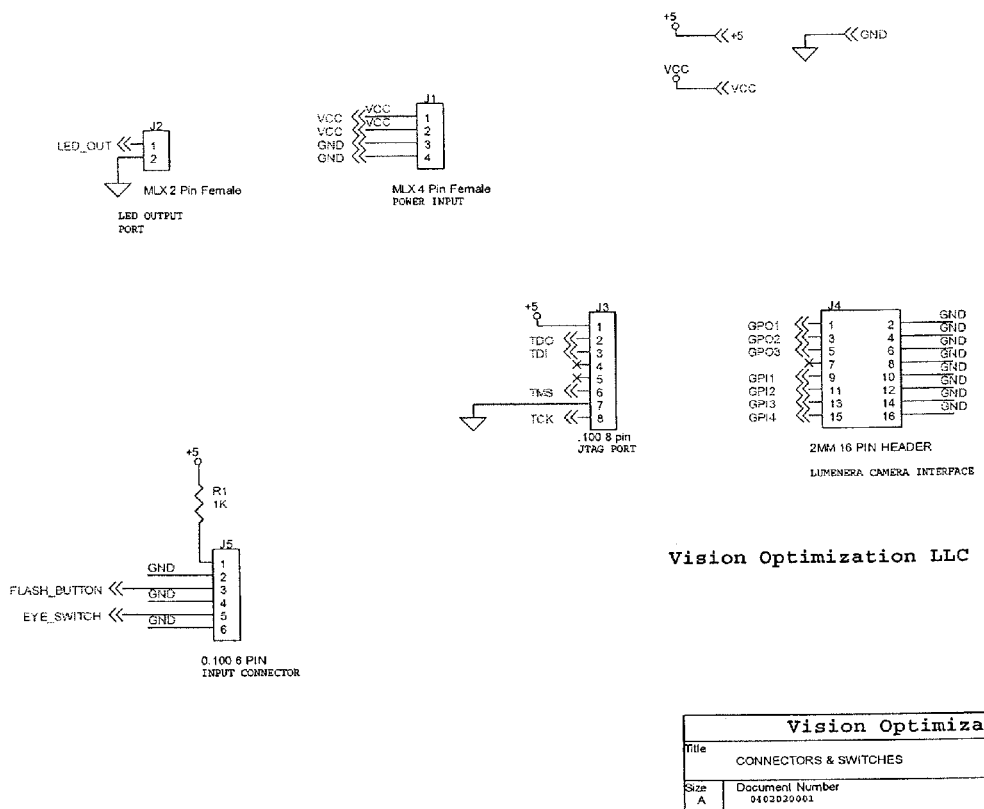
FIG. 24 is a schematic for the connectors and switches in the flash controller of FIG. 23.
Figure 25:
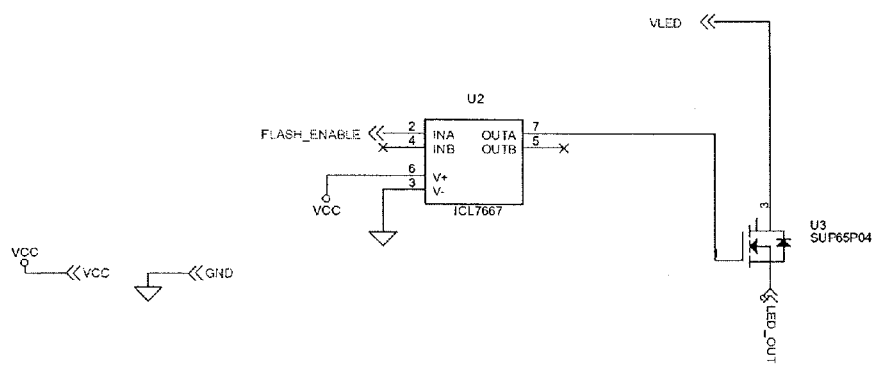
FIG. 25 is a schematic for the LED array drivers in the flash controller of FIG. 23.
Figure 26:
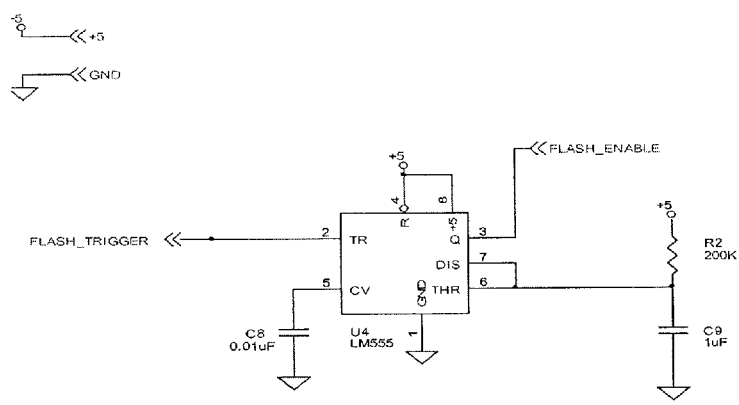
FIG. 26 is a schematic for a one shot trigger in the flash controller of FIG. 23.

According to an exemplary aspect, the RCT system includes software and processing routines that provide what is referred to herein as a selectable 'feature overlay' 2200 as illustrated in conjunction with FIGS. 22(a-d). The feature overlay provides correlative mapping of a visual marker between the display of a raw grid image (FIG. 22b) obtained from an angularly-displaced side-view as described hereinabove and a top-view target elevation or curvature (topography) map (FIG. 22d), for example, generated by the RCT system. An indicia 2210 on the raw grid image can be mapped and displayed as marker indicia 2210' on the elevation or curvature map. This association allows features on the raw target image to be mapped and viewed on the processed topography map. This software feature is useful in identifying where on the processed map physical image features are located. As illustrated by example in FIG. 22, the marker indicia 2210 (2210') is provided by a draw routine in the software. Alternative marking indicia may be provided. According to the exemplary embodiment, there is a 1:1 correspondence between the raw grid image in FIG. 22(b) and the color map shown in FIG. 22(d), but it is a non-linear correspondence obtained, in part, from ray tracing, surface intersections, and relatively complex coordinate transformations. The feature overlay may be provided as a user-selectable option that could be accessed, for example, by a clickable mouse or keyboard stroke.

System Electronics

Flash Controller Electronics

Basically, the flash controller components perform functions related to the grid illumination and digital input/output processing of the system. More specifically, the flash controller components turn the light emitting diode(s) (LED(s)) on and off, provide LED illumination at multiple intensities at a specific light wavelength, and processes digital input/output for switches, indicator lights, etc. Schematics of an exemplary flash controller are shown in FIGS. 22-27.

Figure 29:
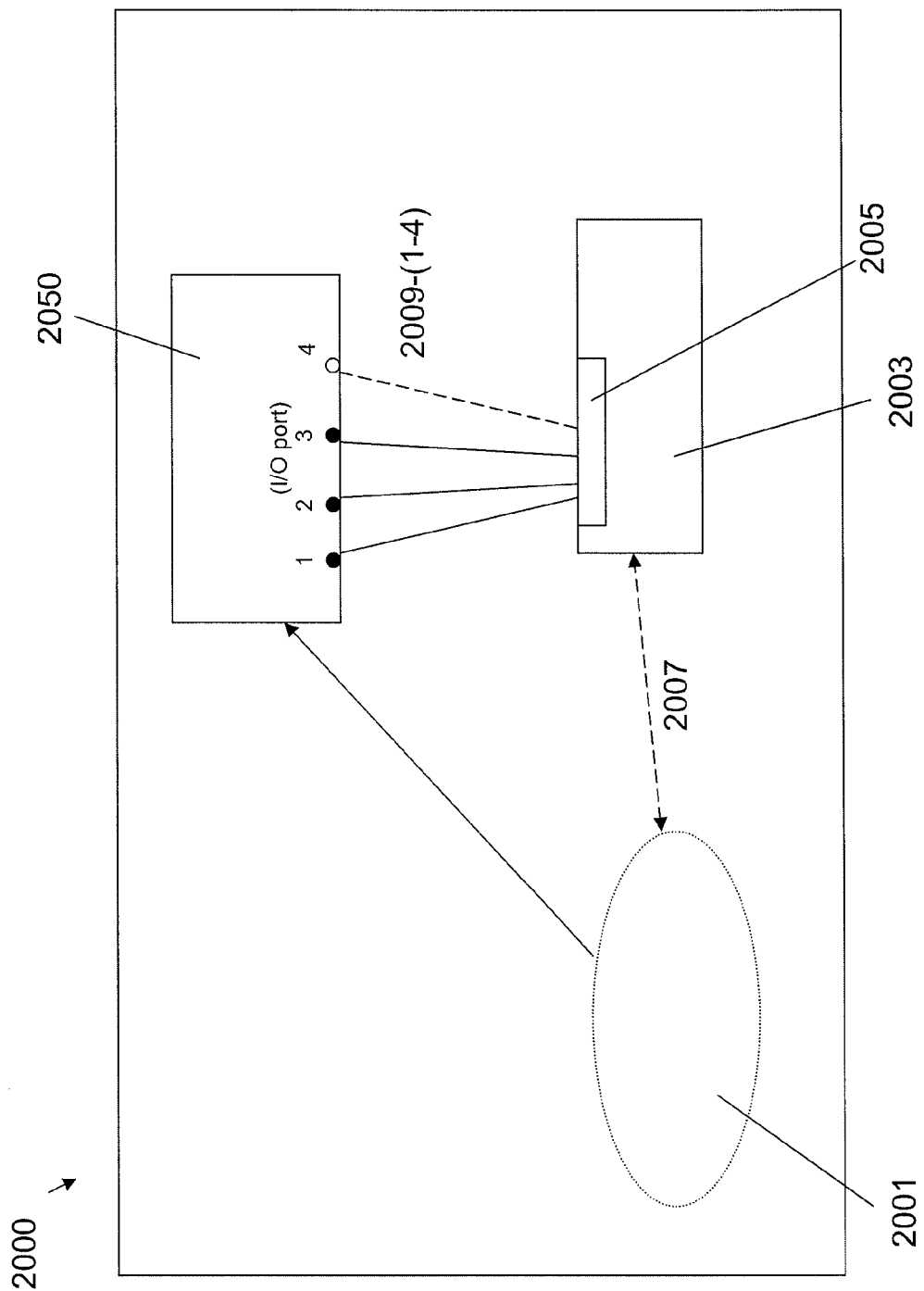
FIG. 29 shows a schematic illustration the advanced RCT system including the flash controller interface according to an exemplary embodiment of the invention.

In further detail, as illustrated schematically in FIG. 29, the flash controller 2003 is designed to accomplished two primary tasks. Primarily, and according to a novel aspect, the flash controller utilizes an available Input/Output (I/O) port (labeled 1-4 in FIG. 29) on the digital camera 2050 of the RCT system 2000 to pass data to and from a host PC 2001 to the flash controller 2003. Secondly, this interface is designed to provide fast communications and be easy to interface with by a programmer.

Figure 27:
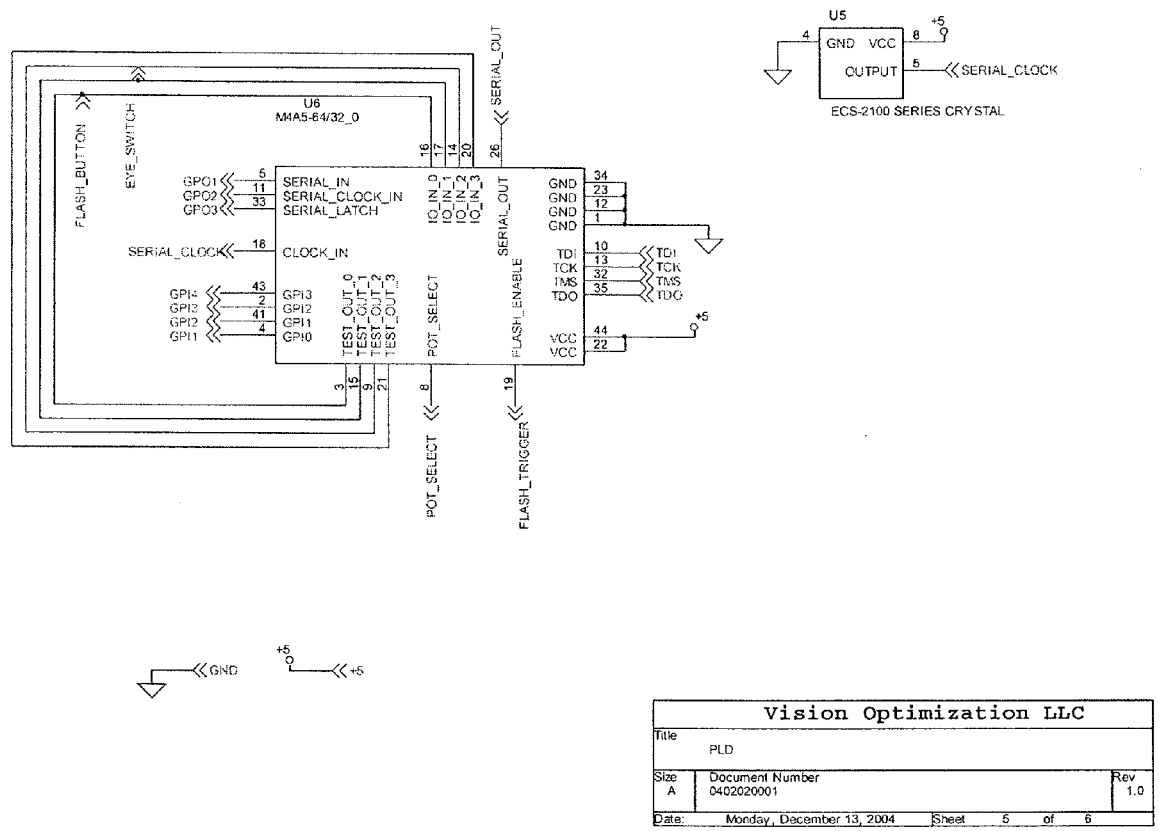
FIG. 27 is a schematic for a programmable logic device (PLD) in the flash controller of FIG. 23.
Figure 28:
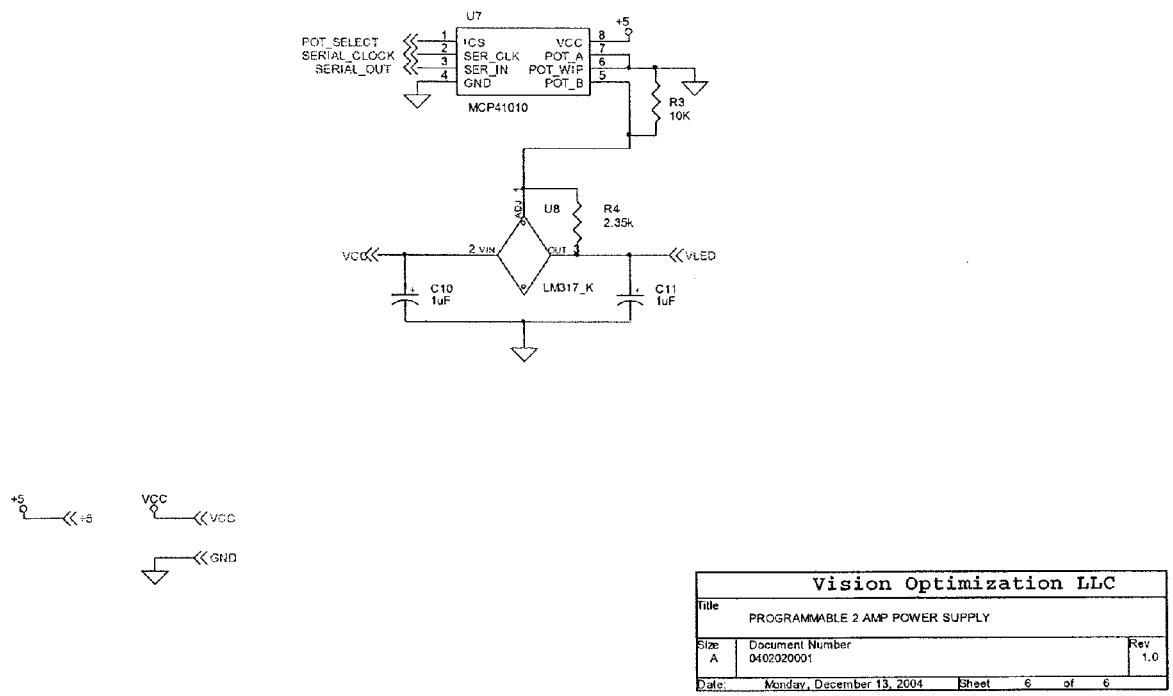
FIG. 28 is a schematic for a programmable current-mode power supply in the flash controller of FIG. 23.

According to an exemplary implementation, the flash controller 2003 utilizes a Programmable Logic Device (PLD) 2005 in FIG. 29 (and as shown in FIG. 27) with software authored in the Verilog Hardware Definition Language (VHDL). The PLD is software configured into a state machine which waits for commands from the PC 2001, executes commands when properly received, and sends data to the PC, as illustrated by arrow 2007.

According to an aspect, the interface utilizes only three I/O wires (1-3, FIG. 29). Data bits are sent serially to the flash controller 2003 from the PC 2001 through the camera I/O port. The three wires (1-3) are implemented as one data clock, one data input, and one data latch to indicate that the full 24 bits have been written. A low to high transition of the data latch causes the flash controller to immediately execute the command requested. 24 bits (3 bytes) are sent for each command. The 3 bytes are formatted as follows:

1) first 8 bits—Flash controller command byte;
2) second 8 bits—Data byte 1 (potentiometer command byte) (MSB out first);
3) third 8 bits—Data byte 2 (potentiometer data byte) (MSB out first).

The first byte is the flash controller command byte. This byte holds the command that the flash controller must immediately execute. The second 2 bytes are data bytes (1 and 2) as further described below. The valid commands that may be issued in the first byte are:

1) Interface Command #1, 0x07—Reset board, data bytes ignored;
2) Interface Command #2, 0x01—data bytes 1 and 2 to potentiometer;
3) Interface Command #3, 0x02—End Potentiometer programming, data bytes ignored;
4) Interface Command #4, 0x04—Set Flash to on, data bytes ignored;
5) Interface Command #5 0x5—Set Flash to off, data bytes ignored;
6) Interface Command #6, 0x06—Clear data input latch, data bytes ignored;
7) Interface Command #7, 0xff—Test Mode, data bytes ignored.

The second two data bytes are the potentiometer interface command (16 bits). Programming of the potentiometer allows the host PC to control the intensity of the flash LED remotely. The first data byte is the potentiometer programming command. The command byte is sent to the board in reverse order (MSB first). The format of this byte is:

| X | X | C1 | C0 | X | X | X | 1 |
|---|---|----|----|---|---|---|---| where X represents a non-specific value. The valid commands that may be sent to the potentiometer are:

| C1 | C0 | Command | Summary |
|----|----|---------|---------|
| 0 | 0 | None | No command executed |
| 0 | 1 | Write | Write data in data byte to potentiometer |
| 1 | 0 | Shutdown | Potentiometer enters shutdown mode (exits shutdown mode when new data byte is written) |

The second data byte is the wiper position to set the potentiometer to, or the resistance value that the potentiometer will be set to, after programming. The format of this byte is:

| D7 | D6 | D5 | D4 | D3 | D2 | D1 | D0 |
|----|----|----|----|----|----|----|----|

These 8 bits allow the potentiometer to be programmed to any of 256 positions. Position 0 is the maximum LED intensity and position 255 is the lowest intensity According to another aspect, in addition to the host PC 2001 sending data to the flash controller 2003, the flash controller can also send data to the host PC. This can be accomplished by utilizing a fourth wire (#4, FIG. 29) of the digital camera I/O port. One wire then additionally is used for an acquire image function button. This button is latched until a specific command (Interface Command #6) is issued. This allows the flash controller to store a button press until the computer is able to read it. Upon writing interface command #6, this data is removed from latch. If a second external event occurs while data is latched, that event is ignored. The other 3 inputs are not latched; data is passed through the PLD 2003 to appropriate camera I/O wires (1-4).

According to an aspect, the flash controller also can execute a test mode function so that the host PC can verify proper operation of the flash controller. Upon entering the test mode, the input data lines will transition to all 1's. The test mode is cleared by writing of interface command #7 (Reset).

According to an aspect, the flash controller also contains a reset mode so that the host PC can return the flash controller to a known state. When a reset is issued, all chips on the flash controller are deselected, the flash LED is turned off, and all test outputs are set to high impedance mode.

Schematics for the voltage power supply (FIG. 22); connectors and switches (FIG. 23); the LED array drivers (FIG. 24); the one shot trigger (FIG. 25); the PLD (FIG. 26); and the programmable 2 AMP current power supply (FIG. 27) are shown.

An exemplary implementation for the flash controller follows:

4 TTL compatible inputs from the host PC.
4 TTL compatible outputs to the host PC.
4 TTL compatible inputs for external events.
2-wire serial interface to potentiometer.
1 flash enable line.
1 chip select output for potentiometer.
1 clock input for potentiometer serial interface.
8-wire JTAG port for programming the PLD chip.

While various embodiments and aspects of the invention have been illustrated, it is to be understood that the foregoing description is not limited to the specific forms or arrangements herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the embodiments of the present invention are adapted to carry out the objectives and obtain the ends and advantages mentioned, as well as those inherent therein. The embodiments, methods, procedures and techniques described herein represent exemplary embodiments and are not intended as limitations on the scope. Changes therein, and other uses, will occur to those skilled in the art, which are encompassed within the spirit of the invention and are defined by the scope of the appended claims.

We claim:

1. A method for making an ophthalmic topography measurement of a target surface including the cornea, the limbus and at least a portion of the adjacent scleral region, comprising:
    conditioning at least a portion of the target surface such that it diffusely reflects an image projected thereon;

projecting a selected image onto a substantial portion of the target surface;
obtaining an image of the diffusely reflected image;
extracting selected features of the image; and
using the extracted features to determine a corneo-scleral surface topography,
wherein the step of extracting selected features of the image comprises
finding the center of the image, referred to as a starting node;
extracting a plurality of horizontal line features from the image to form a horizontal line array;
extracting a plurality of vertical line features from the image to form a vertical line array;
finding an intersection point in the horizontal and vertical line arrays;
finding a plurality of neighboring intersection points in the horizontal and vertical line arrays, wherein each intersection point is a node;
continuing finding a plurality of neighboring intersection points in the horizontal and vertical line arrays until a satisfactory number of intersection points (nodes) have been found to determine the topography of the corneo-scleral surface, further comprising
determining a region of interest (ROI) in the center of the image;
computing a sum of all pixels in a row, saving the sum as computed for all rows, and saving the sum in a row sum array;
computing a sum of all pixels in a column, saving the sum as computed for all columns, and saving the sum in a column sum array;
determining a peak value in the row sum array corresponding to a Y coordinate of a center of a reticle image; and
determining a peak value in the column sum array corresponding to a X coordinate of a center of a reticle image on the image.

2. The method of claim 1, further comprising projecting a grid image.

3. The method of claim 2, comprising projecting a grid image having dimensions that are equal to or greater than 15 mm×12 mm.

4. The method of claim 1, wherein extracting a plurality of vertical and horizontal line features further comprises:
enhancing the vertical line features;
post-processing the vertical line array to thin the vertical lines and remove small noise features;
enhancing the horizontal line features; and
post-process the horizontal line array to thin the horizontal lines and remove small noise features.

5. The method of claim 1, further comprising finding the intersection points in the post-processed vertical and horizontal line arrays.

6. The method of claim 1, further comprising storing an unresolved node in a data structure, wherein an unresolved node has an undetermined x, y pixel location referred to as an indicia 'Point(x, y)'=Point(0, 0).

7. The method of claim 6, further comprising resolving a node by determining an x, y pixel location of said node, and removing each resolved node from the data structure.

8. The method of claim 7, wherein the data structure is a two-dimensional (X×Y) array indexed as an indicia 'Nodes [X, Y]'.

9. The method of claim 8, wherein for each resolved node, Nodes[X, Y]=Point(x,y).

10. The method of claim 9, wherein, when the data structure is empty, predicting the location of a missing node based on the location of found node neighbors.

11. The method of claim 10, further comprising incrementally increasing a search window about a predicted node location until a complete nodal mapping is determined.

12. The method of claim 4, wherein enhancing the vertical and horizontal line features comprises using a convolution operation in the form of a zero-phase finite impulse response filter.

13. The method of claim 12, wherein the dimension of the convolution kernel is (2h+1)×3, where h is the "half-height" of a neighborhood of interest.

14. The method of claim 1, comprising computing a high threshold value, H, and a low threshold value, L, along a one-dimensional profile of each line, wherein H is greater than a 50% scaled value and L is less than the 50% scaled value; and, detecting each local maximum value (peak) as the value exceeding H in a positive manner and each local minimum value (valley) as the value exceeding L in a negative manner.

15. The method of claim 14, comprising dividing each line feature into N equally-spaced sub regions and computing H, L in each sub-region; and, assigning a value of 255 to each peak and a value of zero to all other pixels.

16. The method of claim 5, further comprising assigning the current intersection point a pixel value of "00", where the pixel values in a 2×2 neighborhood in the vertical thinned image are V00, V01, V10, and V11, and the corresponding horizontal thinned image pixel values are H00, H01, H10, and H11, further wherein,
if V00=H00=255, the lines intersect;
if V00=V11=H01=H10=255, the lines intersect; and
if H00=H11=V01=V10=255, the lines intersect.

17. The method of claim 4, further comprising one of manually removing and automatically removing an anomalous node that is at least one of closer to, farther than, and at an angle to, a neighbor that exceeds a predetermined criteria.

18. The method of claim 14, wherein 51%<H<75% and 35%<L<49%.

19. The method of claim 1, further comprising mapping a selectable feature from the diffusely reflected grid image onto a map of the corneo-scleral surface topography.

20. The method of claim 19, further comprising providing a user selectable contemporaneous display of the raw grid image and the map of the corneo-scleral surface topography, wherein the selectable feature on the raw grid image is viewable on the map of the corneo-scleral surface topography.

21. The method of claim 1, wherein the step of obtaining an image of the diffusely reflected image involves obtaining only a single image as a sufficient condition for making an ophthalmic topography measurement of a target surface including the cornea, the limbus and at least a portion of the adjacent scleral region.

22. The method of claim 1, wherein the step of obtaining an image of the diffusely reflected image involves providing a flash controller component that directly interfaces with an Input/Output (I/O) port on a digital camera of the RCT system to pass system control data between a host PC and the flash controller.

23. The method of claim 22, comprising providing only a three wire interface between the flash controller and the camera I/O port, wherein the three wires are implemented as one data clock, one data input, and one data latch.

24. The method of claim 22, further comprising providing a fourth wire interface between the flash controller and the camera I/O port such that the flash controller can send data to the host PC.

25. The method of claim 22, further comprising providing a test mode function so that the host PC can verify proper operation of the flash controller.

26. The method of claim 22, further comprising providing a reset mode so that the host PC can return the flash controller to a known state.

27. A method for making a rasterstereography-based corneo-scleral topography measurement, comprising:
projecting a grid image onto an appropriately conditioned corneo-scleral target surface that diffusely reflects the grid image, wherein the projected grid image has dimensions to overlay substantially the entire target surface;
obtaining an image of the diffusely reflected grid image;
extracting selected features of the imaged grid;
using the extracted features to determine the target surface topography, wherein the step of extracting the selected features of the imaged grid comprises:
finding the center of the imaged grid using histograms of row and columns sums around the center of the image, referred to as a starting node;
extracting a plurality of horizontal line features from the imaged grid to form a horizontal line array, further comprising:
enhancing the horizontal line features; and
post-processing the horizontal line array to thin the horizontal lines and remove small noise features;
extracting a plurality of vertical line features from the imaged grid to form a vertical line array, further comprising:
enhancing the vertical line features; and
post-processing the vertical line array to thin the vertical lines and remove small noise features;
finding an intersection point in the horizontal and vertical line arrays;
finding a plurality of neighboring intersection points in the horizontal and vertical line arrays, wherein each intersection point is a node; and
continuing finding a plurality of neighboring intersection points in the horizontal and vertical line arrays until a satisfactory number of intersection points (nodes) have been found to determine the topography of the target surface.

28. The method of claim 27, further comprising:
determining the center node and finding all connected neighbors of a node;
storing an unresolved node in a data structure, wherein an unresolved node has an undetermined x, y pixel location referred to as an indicia 'Point(x, y)'=Point(0, 0);
resolving a node by determining an (x, y) pixel location of said node, and removing each resolved node from the data structure, wherein the data structure is a two-dimensional (X x Y) array indexed as an indicia 'Nodes[X,Y]', further wherein for each resolved node, Nodes[X, Y]=Point(x,y), further wherein, when the data structure is empty, predicting the location of a missing node based on the location of found node neighbors; and
incrementally increasing a search window about a predicted node location until a complete nodal mapping is determined.

29. The method of claim 27, further comprising:
determining a region of interest (ROI) in the center of the imaged grid;
computing a sum of all pixels in a row, saving the sum as computed for all rows, and saving the sum in a row sum array;
computing a sum of all pixels in a column, saving the sum as computed for all columns, and saving the sum in a column sum array;
determining a peak value in the row sum array corresponding to a Y coordinate of a center of a reticle image on the imaged grid; and
determining a peak value in the column sum array corresponding to a X coordinate of a center of a reticle image on the imaged grid.

30. The method of claim 27, wherein enhancing the vertical and horizontal line features comprises using a convolution operation in the form of a zero-phase finite impulse response filter, wherein the dimension of the convolution kernel is (2h+1)×3, where h is the "half-height" of a neighborhood of interest;
computing a high threshold value, H, and a low threshold value, L, along a one-dimensional profile of each line, wherein H is greater than a 50% scaled value and L is less than the 50% scaled value; and, detecting each local maximum value (peak) as the value exceeding H in a positive manner and each local minimum value (valley) as the value exceeding L in a negative manner;
dividing each line feature into N equally-spaced sub regions and computing H, L in each sub-region; and, assigning a value of 255 to each peak and a value of zero to all other pixels.

* * * * *